(12) United States Patent
Thompson

(10) Patent No.: US 11,827,872 B2
(45) Date of Patent: Nov. 28, 2023

(54) CELL CULTURE MICRODEVICE

(71) Applicant: The University of Adelaide, Adelaide (AU)

(72) Inventor: Jeremy Thompson, Adelaide (AU)

(73) Assignee: The University of Adelaide, Adelaide (AU)

( * ) Notice: Subject to any disclaimer, the term of this patent is extended or adjusted under 35 U.S.C. 154(b) by 0 days.

(21) Appl. No.: 17/782,625

(22) PCT Filed: Dec. 3, 2020

(86) PCT No.: PCT/AU2020/051318
§ 371 (c)(1),
(2) Date: Jun. 3, 2022

(87) PCT Pub. No.: WO2021/108860
PCT Pub. Date: Jun. 10, 2021

(65) Prior Publication Data
US 2023/0013813 A1    Jan. 19, 2023

(30) Foreign Application Priority Data
Dec. 3, 2019 (AU) ................................ 2019904567

(51) Int. Cl.
*C12M 3/06* (2006.01)
*C12M 3/00* (2006.01)
*C12M 1/00* (2006.01)

(52) U.S. Cl.
CPC ............ *C12M 23/16* (2013.01); *C12M 21/06* (2013.01); *C12M 21/08* (2013.01); *C12M 23/42* (2013.01); *C12M 29/10* (2013.01)

(58) Field of Classification Search
CPC ...... C12M 23/16; C12M 23/42; C12M 21/06; C12M 21/08; C12M 29/10
See application file for complete search history.

(56) References Cited

U.S. PATENT DOCUMENTS 5,976,870 A * 11/1999 Park ................... A61M 1/3472
                                                        435/395
2004/0164010 A1    8/2004 Bayer et al.
(Continued)

FOREIGN PATENT DOCUMENTS

DE           19917330 A1    10/2000
WO        2019231977 A1    12/2019

*Primary Examiner* — Michael L Hobbs
(74) *Attorney, Agent, or Firm* — The Watson IP Group, PLC; Jovan N. Jovanovic

(57) ABSTRACT

A cell culture microdevice for maintaining and culturing a cell therein comprising a cell culture unit having at least a first cell carrier unit defining a cell culture chamber formed therein, the first cell carrier unit formed from at least, a chamber base shaped to support the cell thereon, and one or more chamber walls having one or more chamber wall surfaces enclosing the cell culture chamber about a chamber boundary, the first cell carrier unit further providing a guiding surface to guide instruments or fluids into the cell culture chamber located at an aperture through a chamber wall, wherein the cell culture microdevice is configured at a scale to substantially enclose a single cell or cell mass therein. Embodiments of the cell culture microdevice may be suitable for in vitro fertilisation procedures and drug efficacy testing.

16 Claims, 17 Drawing Sheets

(56) References Cited

U.S. PATENT DOCUMENTS

| | | | |
|---|---|---|---|
| 2005/0130254 A1* | 6/2005 | Park | G01N 33/5014 435/40.5 |
| 2010/0247380 A1 | 9/2010 | Lohf et al. | |
| 2014/0308688 A1 | 10/2014 | Grego et al. | |
| 2016/0215246 A1 | 7/2016 | Goh et al. | |
| 2016/0326476 A1 | 11/2016 | Maisch et al. | |
| 2017/0199173 A1 | 7/2017 | Konry et al. | |

\* cited by examiner

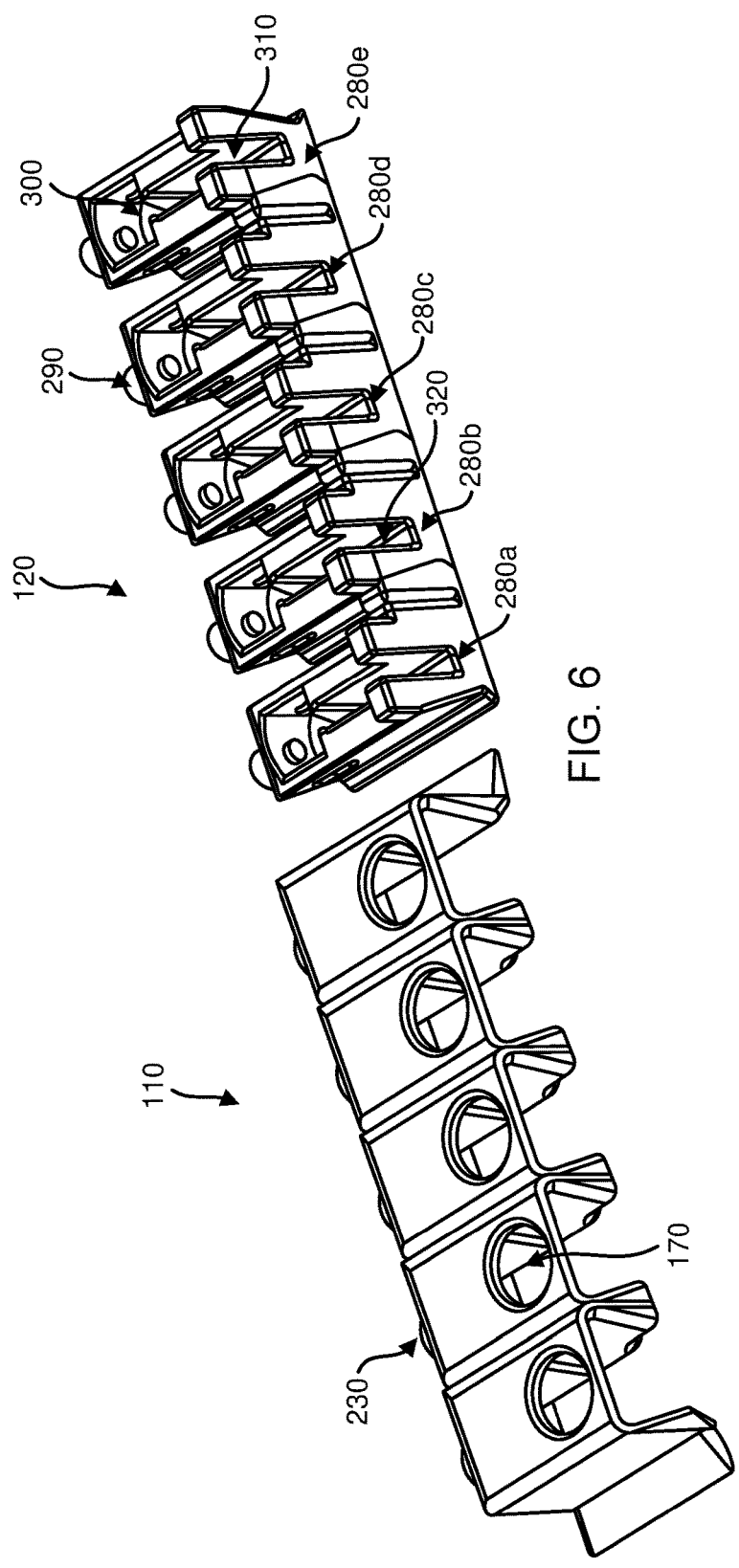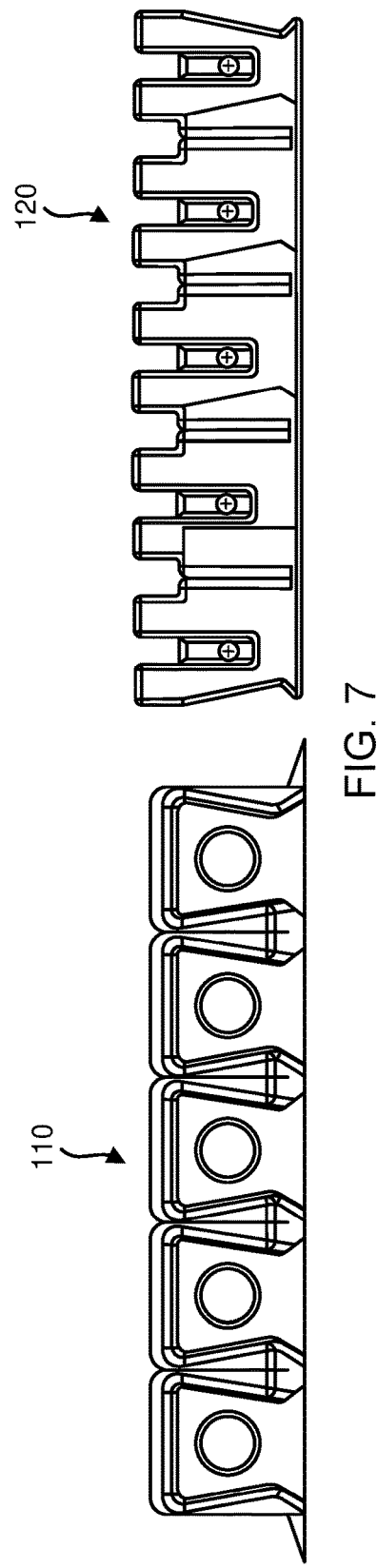

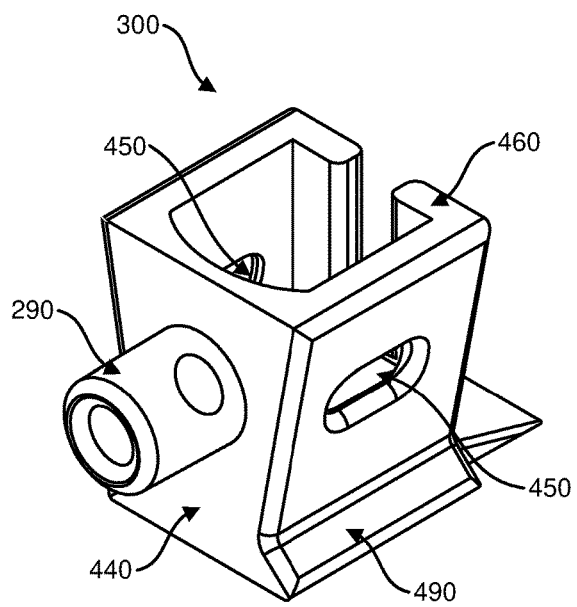 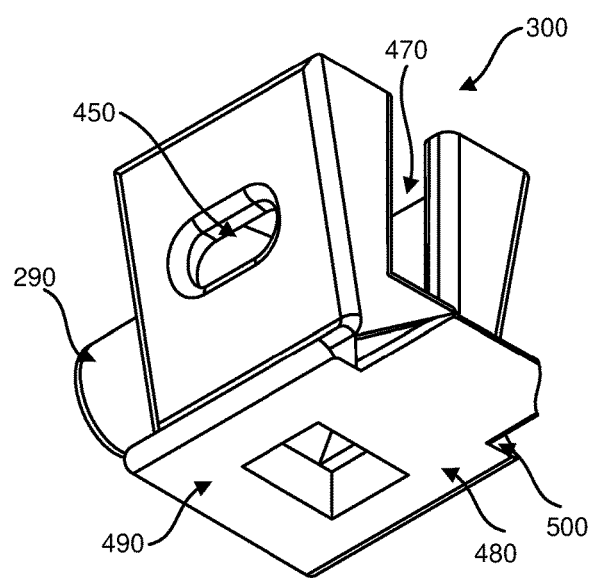
FIG. 9a     FIG. 9b
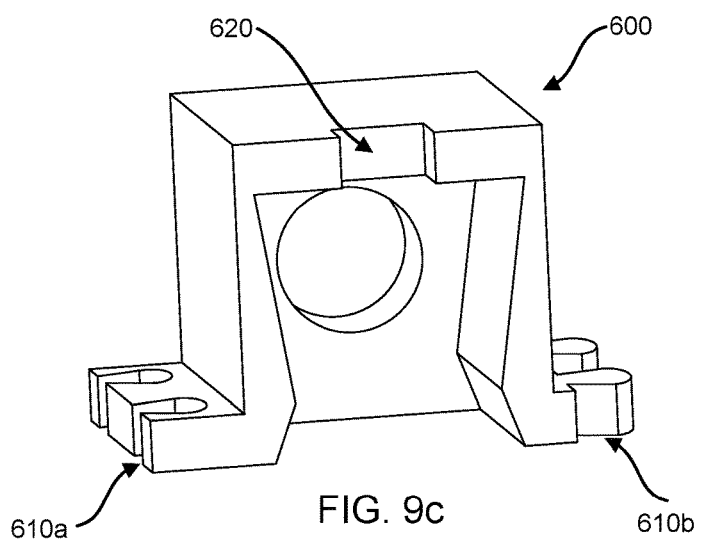
FIG. 9c

CELL CULTURE MICRODEVICE

TECHNICAL FIELD

The technical field generally relates to advances in microdevices for the culture of cells, in particular mammalian cells. The present microdevices are generally of the form of cellular carrier devices, and microdevices for their culture of cells. However, carrier devices are equally applicable to cell culture, stem cell differentiation, cell array assays, infertility treatment, and specifically treatment by in vitro fertilisation (IVF). Specific embodiments relate to microdevices comprising cell culture units, cartridges, arrays, and perfusion devices comprising a cell carrier unit and a cell cover unit.

BACKGROUND

Since the widescale availability of tissue culture microdevices, microscale tissue culture techniques have advanced in sophistication, and their field of use and application have become much more diverse. Microdevices enable the manipulation of cells and their culture environments giving rise to new therapies, products, and processes, many of which are still in their infancy. New microdevices and improvements to existing microdevices such as microfluidic devices, 'culture on a chip' technologies, microscaffolds and micromanipulation devices have given rise to new approaches to 3D tissue engineering, stem cell differentiation, and reproductive medicine as well as ground breaking advances in the success rates of these techniques.

For example, complex in vitro tissue culture was previously limited in success and application by the limited gaseous exchange possible via diffusion, however the development of microcapillary perfusion devices now enables the cultivation and proliferation of larger and more complex tissues. With regard to stem cell culture techniques (and their application), organ culture systems of various embryonic tissues now enable the cultivation of embryonic brain, retina, limb bud, lung, kidney, salivary gland, hair follicle, and tooth cell lines. The application of new tissue engineering techniques, and the microdevices that enable these techniques, will promote new and improved approaches to a number of different therapies.

The potential benefits to the improvements in cellular cultivation and proliferation arising from improved microdevices are significant within the field of reproductive medicine. The nature of the field offers little alternative to in vitro cultivation and manipulation of autologous cells, as these cells must be harvested, expanded, and reintroduced to the patient.

Reproductive assistance by way of in vitro fertilisation (IVF) has become more accessible and has seen recent improvement, and consequently is being accessed by an increasing number of patients. Data released by the Human Fertilisation and Embryology Authority show that, overall, women starting IVF treatment are more likely to have a child than previously'. However, a wide range of variations in the success rates of IVF clinics are observed between individual clinics, with some clinics achieving a success rate as high as 46%, while the rate at others is as low as 10%[1].

The likelihood of success can vary at several stages in the IVF process; during harvest of the ovum, fertilisation of the ovum, development of the early embryo, vitrification of the embryo and transfer of the embryo. The success of ovum selection, fertilisation, embryo development, embryo cryopreservation and preparation for embryo transfer are, currently, largely dependent on the skill of the embryologist.

Factors determinative of a successful IVF pregnancy that occur during the development of the embryo largely involve the physical and environmental conditions present during its growth and development. Any kind of rapid environmental change, physical shock or physical stress that may occur to the sperm, ovum or developing embryo can reduce the likelihood of survival of the embryo and, in turn, its successful implantation for a successful pregnancy.

The physical and environmental conditions of any cell culture system is likely to impact the viability and proliferation of cells in vitro. For instance, selection between scraping (manual/physical), trypsinisation (chemical/enzymatic) and ultrasonic (physical/gentle) for the detachment of adherent cells in preparation for in vivo culture vastly impact the viability of cells and depends largely on the cell type and buffers and other media constituents used.

In tissue engineering, the assembly of functional three dimensional tissue structures during morphogenesis and organogenesis is dependent on intercellular interactions between tissue monolayers. These cell-cell interactions are triggered and maintained by physical and environmental cues within the culture system including the application of mechanical forces, the cellular shape, extracellular matrix geometry or other properties, and physical cell-cell contact and other morphogenic factors. Similarly, the differentiation of stem cells is also directed by many factors within the cell culture matrix, including cell-specific growth factors, enzymes and other proteins, or the depletion or build-up of these constituents or their by-products.

For embryogenesis, the most significant shock or stress to the developing embryo occurs by way of handling and physical manipulation, which are influenced by the embryologist's experience, training, and fatigue. Several events during the growth and preparation of the embryo for IVF procedures involves physical intervention by an embryologist, and therefore presents a risk to the likelihood of success of the embryo and its implantation. The process of harvesting the sperm, ovum and its introduction into an ex-vivo environment presents a risk of stress or shock to the sperm and ovum from both physical injury and detrimental environmental impact during placement in-silico, as well as biochemical stress from placement in a different fluid environment.

The process of fertilisation presents a risk of injury from the physical manipulation required for introduction of the sperm (whether this is intra-cytoplasmic or not). The optimisation of the environment for embryo culture and the removal of the embryo once developed, for cryopreservation or implantation, increases the risk of physical injury. The physical implantation of the embryo also creates an opportunity for physical damage or injury to the embryo. The risk of injury or shock from manipulation and handling, and therefore the success of IVF procedures, is largely influenced by the skill and care of the embryologist as well as the precision of the tools and apparatus that the embryologist has available to them, and the environmental conditions created in the laboratory that are influenced by the embryologist (e.g. sterility, temperature, prevention of any form of contamination, including volatile organic compounds, in addition to the management of parentage identification, to prevent mistaken or mixed parentage).

Precision tools and equipment reduce the likelihood that an embryologist may make errors resulting in injury or shock to the sperm, ovum, or embryo or mistaken parentage. Further, tools or equipment that reduce or eliminate physical interventions or manipulations by the embryologist reduce the likelihood that an event causing physical shock to the sperm, ovum, or embryo may occur. Further, tools or equipment that reduce variation in the optimised ex-vivo environment also reduce biochemical stress to ovum or embryo.

While advances have been made to microinjection devices used in IVF therapies as well as visualisation devices, very little progress has been made for the development of microdevices for handling the cells involved when they must be manipulated, or containing them in a fashion that reduces excessive handling or manipulation.

Typically, the developing embryo is cultured in a large volume of liquid culture medium which minimises the physical impact arising from the depletion of important medium constituents as they are utilised by the cells, and also minimises any physical impact arising from increasing concentrations of waste products in the culture media. However, even very small increases in waste materials and very small decreases in nutrients can impact the developing cells quite significantly. The physical impact of these changes in the composition of culture media during growth are exacerbated by the changing metabolic needs of the embryo during development.

These challenges are akin to those experienced in the development of organoids or complex tissues in vitro. The changing metabolic needs of cell throughout their development into more complex tissues, and indeed tissue structures, introduces more complex requirements of the in vitro tissue culture system.

Containing the physical impact of developmental changes within a contained volume of culture media is not simple. For embryo culture; providing sufficient dilution to minimise the impact of media changes is difficult, as the volume of culture media must remain small enough for the embryo to remain locatable by the embryologist, and larger volumes of media increase the likelihood that the embryo will dilute the known substances produced by the embryo to assist in its own growth or become difficult to locate resulting in over handling or manipulation.

A common approach taken by embryologists to address this issue involves the preparation of a series of culture media through which the developing embryo is cycled throughout its development in vitro. The benefit of this approach is that each culture medium, fertilisation medium or cryopreservation medium can be specifically adapted to the needs of the cells at a particular stage of development or manipulation, however, even with the optimisation of media constituents to meet the requirements of the embryo's growth stage, the stress experienced by the cells in moving from one liquid medium to another still adversely impacts development.

To overcome this problem, various microfluidic and liquid or gaseous perfusion apparatus have been developed with varying degrees of success. Microfluidic 'culture on a chip' microdevices have been developed to utilise microfluidics to move or 'roll' the cell or cell mass from one cell culture 'bath' to the next to prevent cellular shock from excessive manipulation. Other microfluidic devices are adapted to allow for the continual flow of liquid media into and out of a more traditional cell culture dish system, throughout the development of the fertilised ovum to its embryo stage and for preparation for cryopreservation and embryo transfer. These developments have been poorly adopted and many embryologists still tend to prefer static culture techniques utilizing a petri-dish, or variant design of a petri-dish, as embryos are easier to locate and retrieve in these vessels.

Neither approach addresses the need for optimal gaseous exchange, as well as liquid exchanges. In all tissue, and particularly in morphogenesis and stem cell differentiation, adequate aeration by way of gaseous diffusion is critical to development.

Attempts to apply microfluidic techniques to the static culture of embryos have only recently emerged[2]. Researchers are still discovering and optimising techniques that ensure that the ovum and developing embryo do not move excessively, so as to avoid damage or stress, while managing the very small volume of culture medium that can be held within very small channels of microfluidic devices. However, to date, the combination of perfusion within microfluidic devices has not been achieved with any degree of clinical application.

It is well established through the engineering principles established in Richard Feynman's works that the downscaling of engineering systems from the macroscale to the microscale presents a wider spectrum of novel applications, however, it brings about the physical challenges of evaporation, lubrication, heating and inertia which work very differently at such small scales. Engineering design adapted to this scale has not yet been adequately resolved for in vitro cell culture. The present disclosure addresses these issues, at least in part, through design innovation.

It is also well established in the work of Kim Eric Drexler that the use of nano and microscale devices provides opportunities which are not available to macroscale devices. Macroscale cellular devices tend to rely on haphazard interactions between many cells in the hopes that one or more of these interactions will produce the intended results within a predefined margin for acceptance. Microscale devices allow the used to directly interact with the individual cell to target the produce the intended result much more accurately and efficiently. Subsequent interactions are then based on a subject much closer to ideal, to produce more accurate results.

By maintaining the physical stability of the sperm, ovum and embryo within its culture apparatus, the embryologist may more easily and/or accurately handle or manipulate the sperm, ovum or embryo, and minimise the risk of physical shock and/or biochemical stress or further prevent the risk of mixed parentage during fertilisation, embryo culture or embryo transfer. The stabilisation of the cells during culture may improve the success of IVF procedures.

Such approaches may not only resolve difficulties in the successful fertilisation and culture of developing embryos but may also be applicable to the culture of other cell lines sensitive to changing the culture environment in a gradient process.

SUMMARY

In an aspect of the invention, embodiments of the present disclosure relate to a cell culture microdevice for maintaining and culturing a cell therein comprising; a cell culture unit having at least a first cell carrier unit defining a cell culture chamber formed therein, the first cell carrier unit formed from at least, a chamber base shaped to support the cell thereon, and one or more chamber walls having one or more chamber wall surfaces enclosing the cell culture chamber about a chamber boundary, the first cell carrier unit further providing a guiding surface to guide instruments or fluids into the cell culture chamber located at an aperture through a chamber wall, wherein the cell culture microdevice is configured at a scale to substantially enclose a single cell or cell mass therein.

The term 'cell' as used herein is to be understood as interchangeable with the term 'cellular material' and shall refer to a cell, group of cells, tissue, or organoid which is the subject of the invention described herein.

As used herein the term 'cell culture' shall describe any tools or processes in which cellular material is isolated and maintained under controlled conditions for testing, growth, observation, experimentation, harvesting of the culture media, or other biological science processes.

As used herein the term 'microdevice' shall describe fabrications which are produced at a micron scale, for example between 0.1 μm and 1000 μm. Microdevices shall encompass both static and mechanical devices as well as devices in the area of microfluidics.

As used herein the term 'maintaining a cell' shall refer to any process in which cellular material is stored in a controlled environment so as to produce the conditions required for viability. The term 'culturing a cell' shall refer to the processes of cell culture.

As used herein the term 'cryopreservation' shall refer to vitrification or freezing in an interchangeable fashion.

As used herein, the term 'boundary' shall be used to refer to the three dimensional demarcation between the inside of the cell chamber unit and the outside of the cell chamber unit, and may be defined by walls, surfaces, openings and apertures.

In preferred embodiments, the guiding surface will define a curved bottom trench through which instruments will pass and be introduced into the cell culture chamber via the aperture. Alternatively, fluids may be guided by and pass through the curved bottom trench and via the aperture between the inside and outside of the cell culture chamber.

In alternative embodiments, the guiding surface will define a narrow aperture through a chamber wall through which instruments will pass and be introduced into the cell culture chamber via the aperture. Alternatively, fluids may be guided by and pass through the narrow aperture between the inside and outside of the cell culture chamber.

In preferred embodiments, the cell chamber base may be substantially concave. Alternatively, the cell chamber base may be shaped to be substantially convex, stepped, dimpled, or other shapes which may be used to support the cellular material within the cell culture chamber.

The cell carrier unit of aspects of the invention is configured to be formed at microscale. It is also therefore, preferably formed from materials suitable for microscale production which are non-toxic to cells.

One or more chamber walls of certain embodiment may comprise one or more inner wall surfaces sloped towards a proximal point of the chamber so that they are configured to guide the placement of an instrument or a cell within the culture chamber.

In preferred embodiments, the one or more chamber walls of aspects of the invention comprises a proximal wall having a curved inner wall surface configured to guide the placement of an instrument within the culture chamber.

In certain embodiments, the proximal wall may be stepped, dimpled, or otherwise configured to guide the placement of an instrument within the culture chamber.

In preferred embodiments, the cell culture chamber of aspects of the invention is open from above and the chamber base comprises a curved inner surface.

The boundary of aspects of the invention is preferably substantially box shaped with a top opening and a curved proximal wall opposite to the guiding aperture which is able to provide orientation and stability to the cellular material during handling. The cell culture chamber preferably comprises fluid exchange apertures at both the surface of the curved proximal wall and the surface of the culture base. Alternatively, the footprint of the cell culture chamber may be substantially triangular or V-shaped in footprint and sloped towards a proximal point.

In alternative embodiments, the boundary of aspects of the invention may be substantially cylindrical, spherical, triangular, non-symmetrical, or stepped.

In preferred embodiments, the one or more chamber walls of aspects of the invention comprises a proximal wall having a curved inner wall surface configured to guide the placement of an instrument within the culture chamber, and a distal wall defining a distal chamber boundary and having the aperture through the chamber wall formed therethrough, the aperture defining an opening in communication with an elongated guiding portion projecting outwardly from the cell culture chamber having a channel formed therein providing the guiding surface to guide instruments or fluids into the cell culture chamber.

Preferably, the one or more chamber walls of aspects of the invention comprise an intermediate distal wall opposite to the curved proximal wall. The intermediate distal wall comprising the aperture and providing the guiding surface defining a conduit formed perpendicular to the intermediate distal wall, outside of the cell culture chamber.

Preferably, the inner surface of the intermediate distal wall is substantially concave to guide instruments or fluids from the chamber towards the guiding surface. Alternatively, the inner surface of the intermediate distal wall may be flat.

In preferred embodiments, the one or more chamber walls of aspects of the invention comprises at least a left side wall and a right side wall each having a left side aperture and a right side aperture formed therethrough.

In preferred embodiments, the proximal wall of aspects of the invention has a proximal aperture formed therethrough, configured in horizontal alignment with the guiding surface to ease the flow of fluid through the cell culture chamber between the aperture and the proximal aperture.

In preferred embodiments, the aperture of aspects of the invention is configured for perfusion therethrough. Preferably, the aperture is located through the chamber base and is sized such that the cell cannot pass therethrough. Alternatively, the aperture is located through a chamber wall or made up of several apertures distributed over one or more surfaces of the boundary.

In preferred embodiments, the proximal wall of aspects of the invention comprises a perfusion inlet opening adapted for fluid perfusion therethrough, and a tubing fitting configured for engagement of a perfusion tube to the perfusion inlet opening.

Alternatively, the tubing fitting may be configured for engagement of a perfusion manifold or other means of supplying perfusion media.

The fluid exchange apertures may alternatively be located on other surfaces, may be integrated into other apertures and openings, or may not be required for maintenance and culturing of the cellular material in some cases.

In preferred embodiments, the first cell carrier unit of aspects of the invention comprises a cell chamber wall having an exterior wall coupling adapted to engage with a corresponding exterior wall coupling on at least a second cell carrier unit, thereby forming a cell carrier array. Preferably, the cell carrier array may comprise an unlimited number of cell carrier units, each adapted to engage with another. Preferably, the cell carrier array will be a linear array in the horizontal plane, but alternatively may stack in the vertical plane or a mixture of both. Preferably, the cell carrier units will clip together in the horizontal plane and stack in the vertical plane or alternatively may slidably engage together in either the horizontal or vertical plane.

In certain embodiments, the cell culture microdevice of aspects of the invention comprises at least a second cell carrier unit formed integrally with the first cell carrier unit, thereby forming a cell carrier cartridge. Preferably, the cell carrier cartridge may comprise an unlimited number of cell carrier units, each in integral connection with another. Preferably, the cell carrier cartridge will be linear in the horizontal plane, but alternatively may produce a cartridge in the vertical plane or a mixture of both. In preferred embodiments, the cell carrier cartridge may stack or engage with another cell carrier cartridge to define a cell carrier cartridge array.

In alternative embodiments, cell culture arrays and cell culture cartridges may be formed as a circular array or cartridge or in another form that may adapt the array or cartridge for further processing.

In preferred embodiments, the cell culture microdevice of aspects of the invention further comprises a first cell cover unit having a first cover wall configured to cover at least a portion of the opening from above of the cell culture chamber when the first cell cover unit and the first cell carrier unit are connected to form a cell culture unit base.

In preferred embodiments, the cell cover unit will be shaped to substantially surround the cell carrier unit on three surfaces, including the top surface, and entirely cover the top opening when located thereon.

In alternative embodiments, the cell cover unit may be shaped to substantially cover at least one surface of the cell carrier unit.

Preferably, the cell cover unit has at least one edge configured to terminate with a portion capable of engaging with the cell carrier unit of aspects of the invention. Preferably, the portion capable of engaging with the cell carrier unit is adapted to engage with the base of the cell carrier unit thereby forming a cell culture base. In a further preferred form, the cell cover unit is configured to slidably engage with the base of the cell carrier unit.

In preferred embodiments, the first cell cover unit of aspects of the invention comprises an exterior wall coupling adapted to engage with a corresponding exterior wall coupling on at least a second cell cover unit, thereby forming a cell cover array. Preferably, the cell cover array may comprise an unlimited number of cell cover units, each adapted to engage with another. Preferably, the cell cover array will be a linear array in the horizontal plane, but alternatively may stack in the vertical plane or a mixture of both. Preferably, the cell cover units will clip together in the horizontal plane and stack in the vertical plane or alternatively may slidably engage together in either the horizontal or vertical plane.

In preferred embodiments, the cell culture microdevice of aspects of the invention further comprises at least a second cell cover unit formed integrally with the first cell cover unit, thereby forming a cell cover cartridge. Preferably, the cell cover cartridge may comprise an unlimited number of cell cover units, each in integral connection with another. Preferably, the cell cover cartridge will be linear in the horizontal plane, but alternatively may produce a cartridge in the vertical plane or a mixture of both. In preferred embodiments, the cell cover cartridge may stack or engage with another cell cover cartridge to define a cell cover cartridge array.

In preferred embodiments, the first cell cover unit and the first cell carrier unit of aspects of the invention define a cell culture unit base. In preferred embodiments, the cell culture unit base is defined by the first cell cover unit and the first cell carrier unit terminating on a flat bottom surface to provide a stable support. Alternatively, the cell culture base may be defined by one of the first cell carrier unit or the first cell cover unit in one configuration and the other in another configuration.

In a preferred form, the cell culture base is adapted to connect with another cell culture cartridge, cell carrier unit or cell cover unit. The base is preferably configured to physically stabilise the cell carrier unit, when placed upon a surface or when connected with another component or apparatus.

In preferred embodiments, the first cell cover unit of aspects of the invention is configured to slidably engage with the first cell carrier unit. In preferred embodiments, the first cell cover unit is shaped to slidably engage with each of the two sides of the first cell carrier unit perpendicular to the proximal-distal axis.

In certain embodiments, the first cell cover unit comprises a media inlet configured to engage a tubing fitting on the first cell carrier unit and allow the perfusion tubing to attach to the tubing fitting thereon. Alternatively, the media inlet may be configured to engage a perfusion manifold or other means of supplying perfusion media.

In preferred embodiments, the first cell cover unit further comprises an access aperture formed therethrough, the access aperture formed through the first cell cover unit is configured to permit access to the opening from above in a first position and cover at least a portion of the opening from above in a second position, and is adapted to slidably engage the first cell carrier unit from the first position to the second position.

In preferred embodiments, the access aperture is the same size and shape of the top opening such that the top opening is wholly accessible through the access aperture. In alternative embodiments, the access aperture may be larger than the top aperture, and of a sloped shape to guide instruments or the cell into the cell culture chamber when configured for access.

In certain embodiments, an exterior surface of the chamber base of aspects of the invention comprises a notch configured to receive a lug projecting outwardly from a cell carrier unit or a cell cover unit.

A method of use of the cell culture microdevice of aspects of the invention comprising the steps of; placing at ease one cell within the cell culture chamber of the cell culture microdevice, and culturing the cell therein.

A method of use of the cell culture microdevice of aspects of the invention comprising the steps of; obtaining instructions for constructing the cell culture microdevice, and executing the instruction in an additive manufacturing process.

In preferred forms of aspects of the invention, the cell culture unit comprises at least four walls and a base defining a cell culture chamber therein. The at least four walls preferably comprises a proximal wall having a curved inner surface defining the cell culture chamber wherein the curvature provides a point of reference for orienting a cell handling apparatus, a left side wall, a right side wall and an intermediate distal wall. In preferred embodiments, the intermediate distal wall comprises an opening formed therethrough, an inner surface defining the cell culture chamber, and an outer surface having a channel formed substantially perpendicularly thereto. The channel is preferably formed by an inner surface of the left side wall and an inner surface of the right side wall extending distally beyond the intermediate distal wall and terminating substantially perpendicularly to an exterior distal wall having an opening formed therethrough.

The opening formed in the intermediate distal wall, by the channel, and in the exterior distal wall are preferably aligned to provide a line of sight from a distal end of the cell culture carrier to the cell culture chamber. This alignment preferably provides guidance for an embryologist or other users to carefully introduce instruments, such as micropipettes, into the cell culture chamber to access cells with little interference or disruption to the cells.

For instance, an embryologist seeking to remove an embryo from the cell culture chamber for implantation may introduce a micropipette through the exterior distal wall opening, they may run and/or cradle the micropipette tip upon the channel until the micropipette reaches the curved inner surface of the proximal wall. The curvature of the proximal wall guides the micropipette to the centre of the cell culture chamber, at which time the embryologist may gently aspirate or inject the embryo cells and media directly beneath the micropipette. The conformation of the cell culture carrier which provides physical support for instruments such as micropipettes, and guidance for the placement or positioning of instruments, reduces the impact of errors made by the operator which may injure cells or impede their optimal growth. The conformation of the cell culture carrier therefore optimises culture techniques and in turn cell viability, and reduces the impact of user error.

Preferably, the left and/or right side walls comprise an overflow opening formed therethrough. Preferably, the proximal wall comprises an inlet opening defined by an inlet fitting located on the outer surface of the proximal wall. The inlet fitting may act as a connector for tubing or other instruments. It may connect with tubing used to transfer fluid into the cell culture unit to perform a perfusion culture. The inlet fitting may also connect with tubes or the like which are simply used as a point of reference for the location of the cell culture unit or a holder to maintain the cell culture unit in place.

In a further preferred form, the inlet opening, the intermediate distal wall, the channel and in the exterior distal wall are preferably aligned to provide a line of sight from the distal wall through the cell culture carrier and through the inlet opening. Line of sight alignment through the cell culture carrier is preferably adapted to enable cells to be cultured during a perfusion of culture media through the cell culture unit. Preferably, a base of the cell culture chamber is at least partially below the line of sight through the cell culture carrier. This configuration minimises physical disruption to cells in culture from turbulence or current caused by fluid perfusion.

Perfusion techniques may optimise conditions for the growth of certain cell types, particularly for cells that are sensitive to biochemical changes in culture media, which may arise from the depletion of nutrients or increase in waste product in culture media, or those that may have varying biochemical requirements as the cells are cultured through different growth phases. Embryo culture for IVF procedures may benefit from perfusion culture, as may the culture of complex structures such as valve structures or organoids, skin, liver, kidney, lung or other tissue grafts, or complex cell lines such as bone marrow or stem cells, or for the culture of any cell line for patients susceptible to tissue rejection.

Broad embodiments of the invention now will be described with reference to the accompanying drawings together with the Examples and the preferred embodiments disclosed in the detailed description. The invention may be embodied in many different forms and should not be construed as limited to the embodiments described herein. These embodiments are provided by way of illustration only such that this disclosure will be thorough, complete and will convey the full scope and breadth of the invention.

BRIEF DESCRIPTION OF THE FIGURES

FIG. 6 shows a top perspective view of an unassembled cell culture array or cartridge according to embodiments of the invention.

FIG. 7 shows a rear view of an unassembled cell culture array or cartridge according to embodiments of the invention.

FIGS. 9a and 9b show a cell cradle portion of a cell culture unit carrier according to embodiments of the invention. FIG. 9a shows a top perspective view and FIG. 9b shows a bottom perspective view. FIGS. 9c, 9d and 9e show an unassembled cell unit cover and an unassembled cell culture array. FIG. 9c shows a rear perspective view of an expandable cell unit cover, FIG. 9d shows a rear perspective view of an expandable cell culture array, and FIG. 9e shows a bottom rear perspective view of an expandable cell culture array.

FIG. 10a shows a top front perspective view and FIG. 10b shows a top rear perspective view. FIG. 10c shows a top front perspective view of a cell culture unit carrier according to an alternative embodiment.

FIG. 11a shows a rear view, FIG. 11b shows a front angle view, and FIG. 11c shows a bottom perspective view.

FIG. 15a shows percentage embryo development in the presence of microdevices according to the invention and their media, FIG. 15b shows percentage embryo development in the presence of microdevices according to the invention, and FIG. 15c shows percentage DNA repair.

FIGS. 17a to 17c show embryo development under static culture conditions at each day of development to Day 5 according to media type and intervention, FIG. 17e shows percentage DNA repair within the same groups.

FIGS. 18a to 18d show changes in embryo development over time when exposed to varying oxygen concentrations.

Several embodiments of the invention are described in the following examples.

DESCRIPTION OF PREFERRED EMBODIMENTS

Cell culture microdevices as described in the following embodiments are generally constructed from a single cell culture unit having a unit carrier and a unit cover, an array of repeating units engaged to form a cell culture array having an array carrier and an array cover, or a cartridge of repeating units integrated to form a cell culture cartridge having a cartridge carrier and a cartridge cover. They will each be generally referred to below as a 'carrier' and 'cover' when they may take any of these forms, that being as a single unit, an array of repeating units of any shape or number, or a cartridge of repeating units of any shape or number.

Those skilled in the art will understand the benefits of manufacturing the 'carrier' and 'cover' embodiments in unitary format, formats able to be engaged in an array, and formats which integrally contain multiple 'carriers' or 'covers'. While one of these formats may be referred to in each of the embodiments below, it is to be understood that the other formats may be substituted under certain circumstances.

EXAMPLE 1

Cell Culture Array

Figure 1:
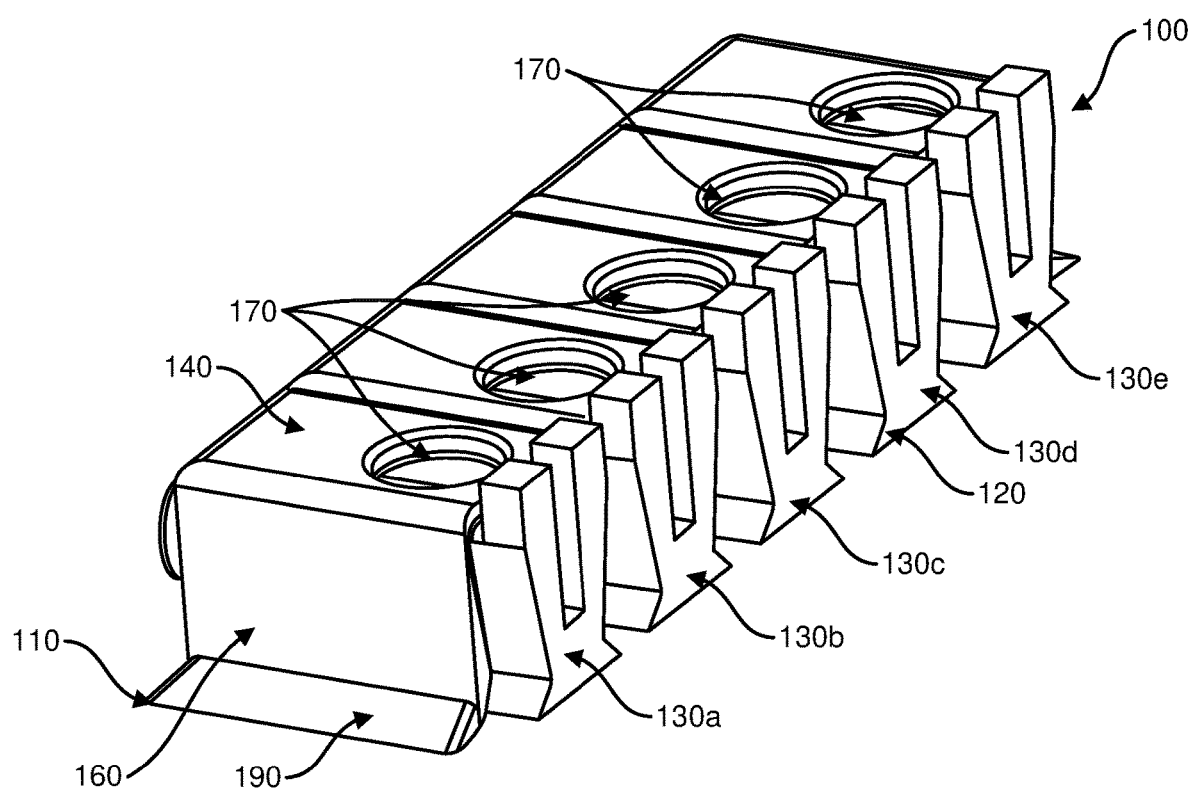
FIG. 1 shows a top perspective view of an assembled cell culture array or cartridge according to embodiments of the invention.

FIG. 1 illustrates an assembled cell culture array 100 having an array cover 110 placed upon an array carrier 120. FIG. 1 depicts a linear cell culture array having five repeating cell culture units 130a, 130b, 130c, 130d and 130e arranged side by side. The linear array cover 110 is configured such that each unit cover is adjacent to the next forming a flat surface across the top exterior of the array cover 110 having a slight groove therein between each unit cover. The cover is formed from four walls including a rectangular planar top wall 140 terminating at either end in a planar left end wall 150 (not shown) and a planar right end wall 160 formed at 90 degrees and extending downwardly from the top wall 140. A series of annular openings 170 is formed through the top wall 140 across the length of the top wall; one opening is formed through the top wall of each unit cover. The left end wall 150 (not shown) and the right end wall 160 terminate at their bottom edge with a left base flange 180 (not shown) and a right base flange 190.

The left base flange and the right base flange may be configured to engage with other components such as robotics equipment, culture dishes, additional cell culture units or other laboratory equipment; or they may be configured, as depicted in FIG. 1, to simply provide the cell culture array 100 with stability when placed thereon.

Figure 2:
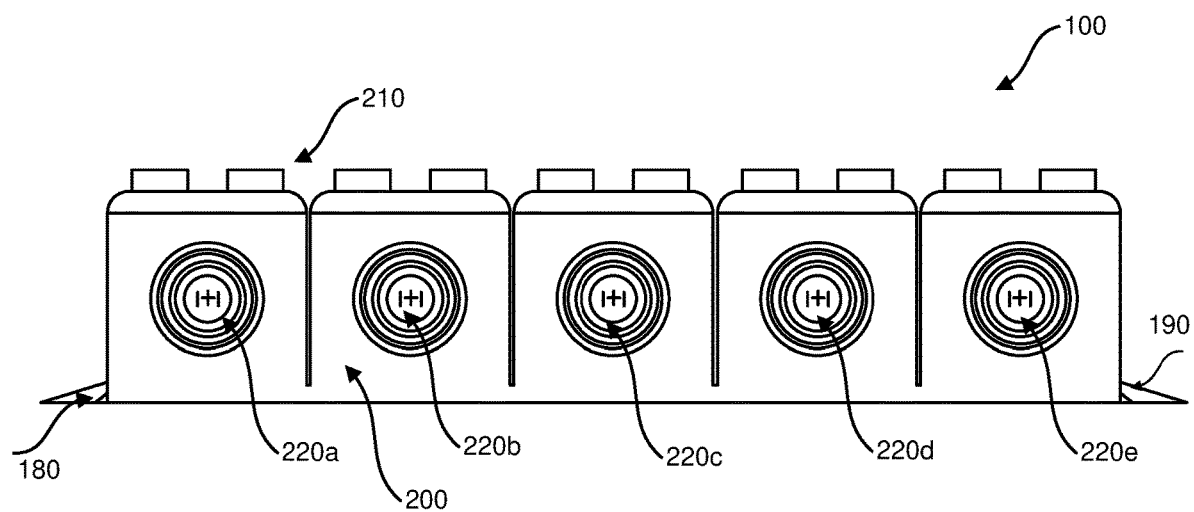
FIG. 2 shows a front view of an assembled cell culture array or cartridge according to embodiments of the invention.

In addition to the top wall, the left end wall and the right end wall, the array cover 110 further includes a front wall. FIG. 2 illustrates the front wall 200 of the array cover 120. A rectangular planar front wall 200 of array cover 120 extends downwardly from the top wall 140 at about 90 degrees and extends between a front edge of left end wall 150 and a front edge of right end wall 160. The bottom edge of the front wall 200 is level with the bottom edge of the left end wall 150 and the bottom edge of the right end wall 160. A vertical groove 210 within the front wall 200 defines one unit cover from the next, and extends through the array cover forming a continuous groove within the top wall. A series of annular openings 220a, 220b, 220c, 220d and 220e is formed through the front wall 200 across the width of the top wall, as one opening is formed through the front wall of each unit cover. Each annular opening is defined by an annular connector 230 protruding from the surface of the front wall. The annular connector may be configured to connect with any number of different apparatus, but most commonly is a simple silicon tubing connector able to create a fluid seal with a silicon tube.

Figure 3:
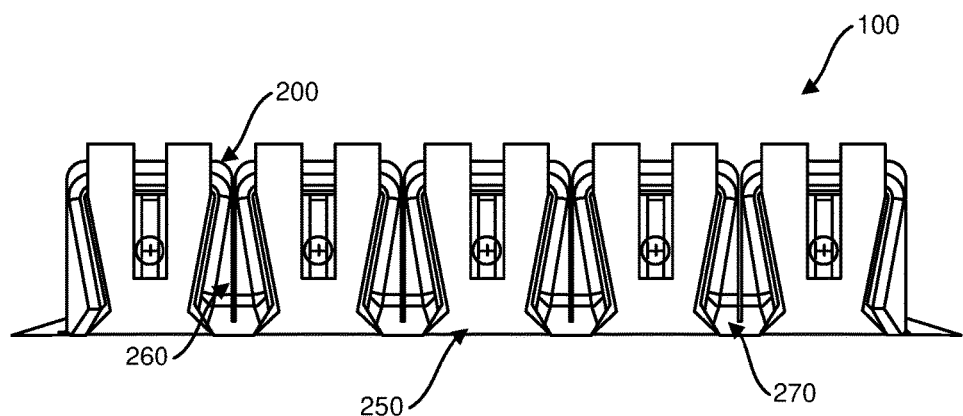
FIG. 3 shows a rear view of an assembled cell culture array or cartridge according to embodiments of the invention.

FIG. 3 shows the open back of the array cover 100 having an array carrier 250 located therein. Vertical grooves 210 between each unit cover within the array cover extend through the array cover between internal walls 260 that complete the form of each unit cover within the array cover. As illustrated in FIG. 3, the internal walls 260 forming each unit cover are shaped or formed to fill the space between adjacent unit carriers to minimise the gap between the unit carrier and the unit cover, so that the shape of the unit cover is able to guide the sliding placement of the unit carrier, and also to minimise the gap between the outer wall surface of each unit cover. When formed in an array, the repeating nature of this configuration ensures that each unit carrier of the array carrier is able to easily slide into the desired position with respect to the array cover and become securely positioned therein.

A sliding mechanism 270 is provided at the bottom edge of each unit cover wall to reversibly and securely connect one unit cover with the next to form the array cover. The sliding mechanism allows individual cell culture units to be assembled in the form of an array, but also to be easily separated from one another so that one cell culture can be handled differently to another, with minimal disruption or interference (from unnecessary handling) of the cells in culture.

Figure 4:
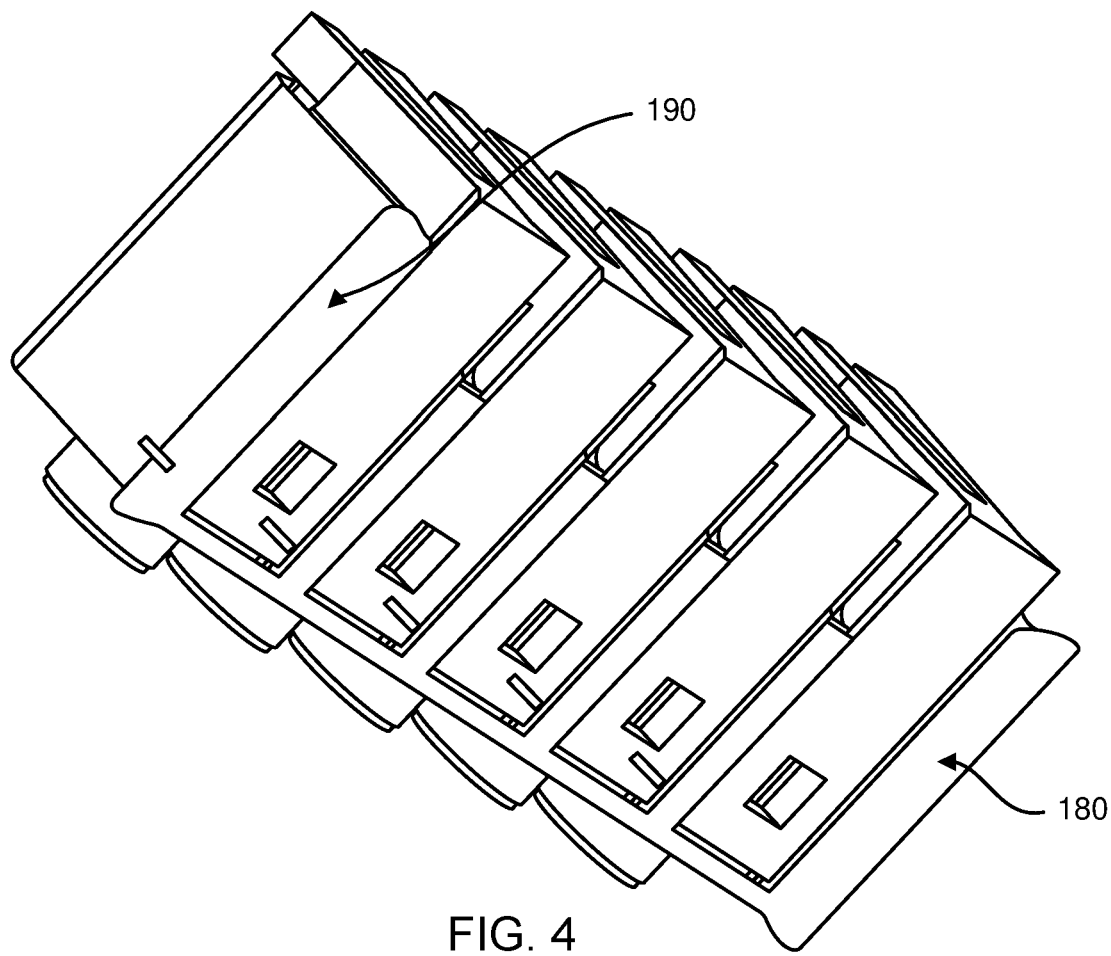
FIG. 4 shows a bottom perspective view of an assembled cell culture array or cartridge according to embodiments of the invention.
Figure 5:
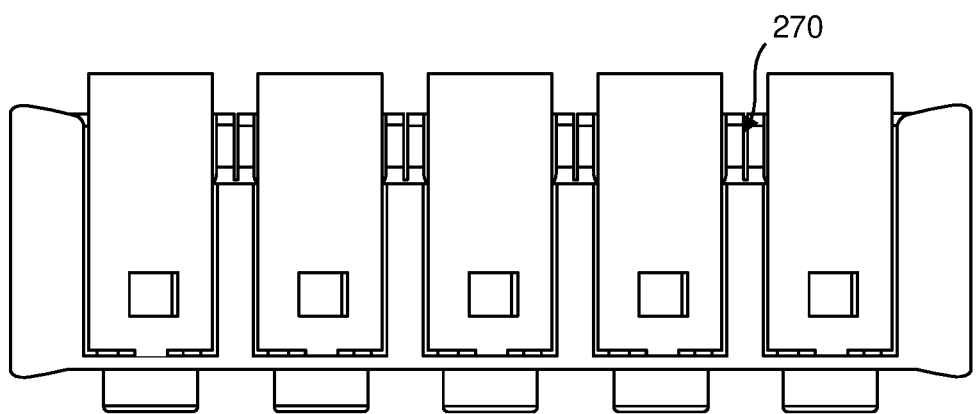
FIG. 5 shows a bottom view of an assembled cell culture array or cartridge according to embodiments of the invention.

FIGS. 4 and 5 show the base of the cell culture array; by way of a perspective view at FIG. 4, and by way of a direct view at FIG. 5. The Figures illustrate the configuration of the bottom surface of the array carrier showing the internal walls of the individual unit covers and the shape of the base flanges; the left base flange 180 and right base flange 190. The sliding mechanism 270 extends through only a portion of the internal walls of the individual unit covers.

Figure 8:
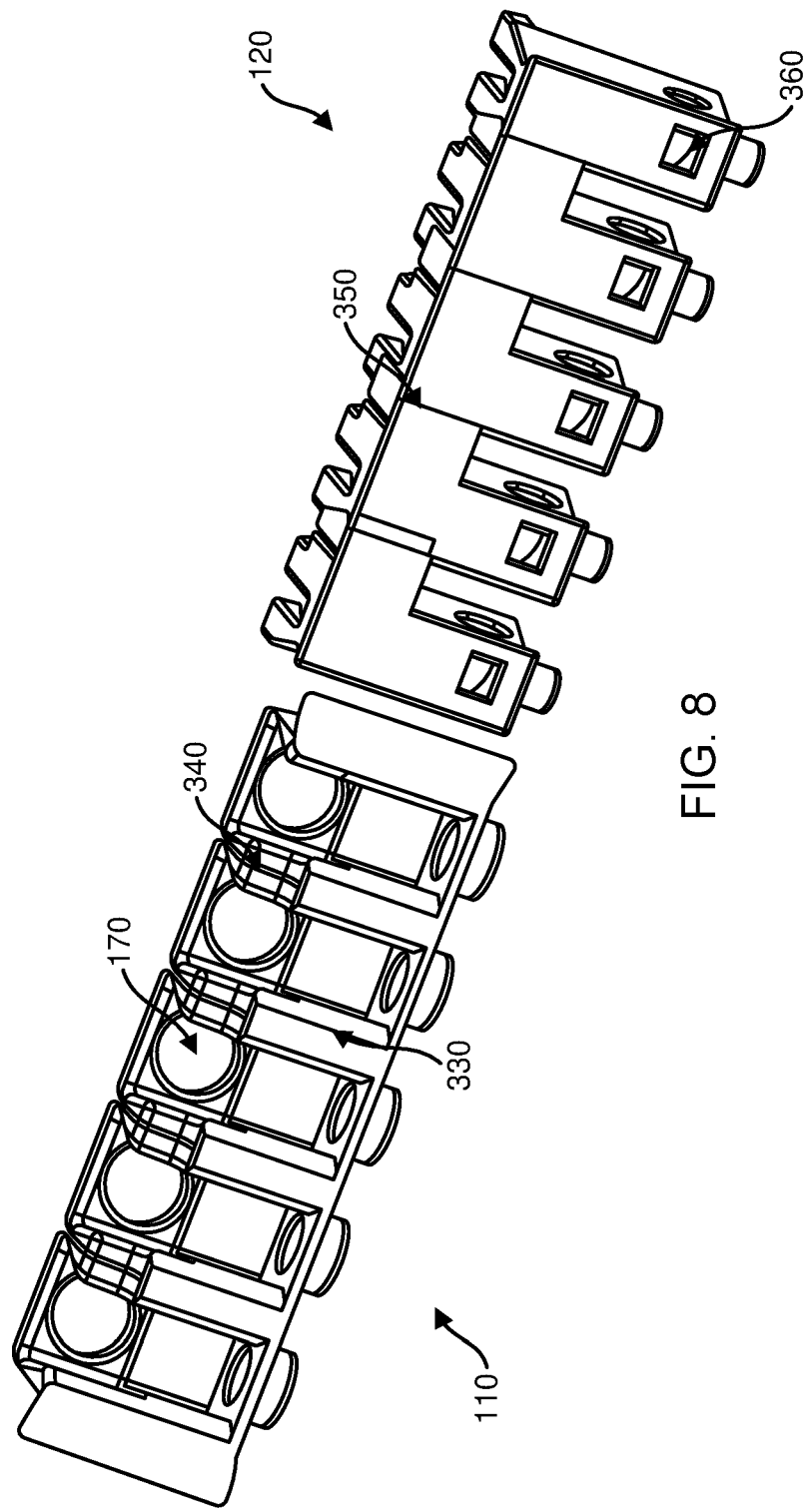
FIG. 8 shows a bottom perspective view of an unassembled cell culture array or cartridge according to embodiments of the invention.

FIGS. 6, 7 and 8 illustrate the array cover and the array carrier separately, side by side, and provide a top perspective view, a rear view, and a bottom perspective view, respectively. With reference to FIG. 6, the array carrier 120 is formed from a linear cell culture array carrier having five repeating unit carriers 280a, 280b, 280c, 280d and 280e arranged side by side. Each unit carrier comprises a media inlet 290 protruding from the exterior front surface of the unit carrier, a cell cradle 300 formed within the unit carrier and a guide channel 310 formed between the cell cradle and the exterior of the unit carrier 280. Media inlet 290 allows for the perfusion of liquid media (or other fluids) into or through the cellular environment within the carrier. Fluids can also flow from the cellular environment within the carrier through the guide channel 310 to the outside of the unit carrier through channel outlet 320. FIG. 7 illustrates the alignment of the base of channel outlet 320, the bottom surface of guide channel 310 and the aperture formed by media inlet 290. FIG. 7 shows that a clear line of sight is formed through these openings, consequently any turbulence caused during cellular perfusion through media inlet 290 is unlikely to impact cellular growth in cell cradle 300.

FIGS. 6 and 7 illustrate the relative size of annular connector 230 of array cover 110 with respect to media inlet 290 of array carrier 120. The exterior surface of media inlet 290 is configured to be slightly smaller than the interior surface of annular connector 230. Thereby, upon sliding of the array cover upon the array carrier, the exterior surface of the media inlet 290 is able to fit quite closely to the internal surface of the annular connector 230. Fluids may thereby pass through the annular connector and the media inlet without leakage of the fluid through these points of contact.

FIGS. 6 and 8 illustrate the positioning of annular opening 170 through array cover 110 with respect to array carrier 120. Turning to FIG. 8, sliding mechanism 270 is further illustrated as consisting of runner 330 located between individual unit covers of array cover 110 terminating prior to gap 340 between the individual unit covers of the array cover toward the rear of array cover 110. The runner 330 and gap 340 of array cover 110 engage with slider 350 on unit carrier 120. When placed in an overlapping manner, slider 350 slides upon runner 330 and is guided by the space permitted for sliding of the slider 350 between individual unit covers. Sliding stops when slider 350 reaches gap 340 and may rest in a closed position therein. In an open position, slider 350 is in contact with runner 330. In this position, annular opening 170 is positioned above cell cradle 300 and is located in correct alignment the cell cradle 300 for optimal placement of the ovum or other cell at the centre of the cradle from above. In a closed position, slider 350 is moved and stopped within gap 340, whereby annular opening 170 is entirely located above guide channel 310 and cell cradle 300 is covered from above. Cradle outlet 360 is also illustrated in array carrier 120 of FIG. 8. This feature is optional, however, where provided, it allows additional access to the cell cradle to enable removal or transfer of the embryo or its surrounding media.

The Figures illustrate a linear array configuration, however, as would be readily apparent to persons skilled in the art, the array configuration may be extended beyond five units and may also be readily adapt to array configurations that are non-linear. For instance, the linear array configuration may be readily adapted to a circular array, which may be more readily amendable to automated or robotic handling techniques. For instance, a circular array may be mounted on a carousel an in turn mounted within microscopic or other visualisation apparatus. A carousel arrangement may be more readily accessible by operators, handheld apparatus, or robotics apparatus for pipetting, for the introduction of vacuum manifolds, for the introduction of pump systems or for implementation of cryopreservation processes.

EXAMPLE 2

Cell Culture Unit

Figure 9D:
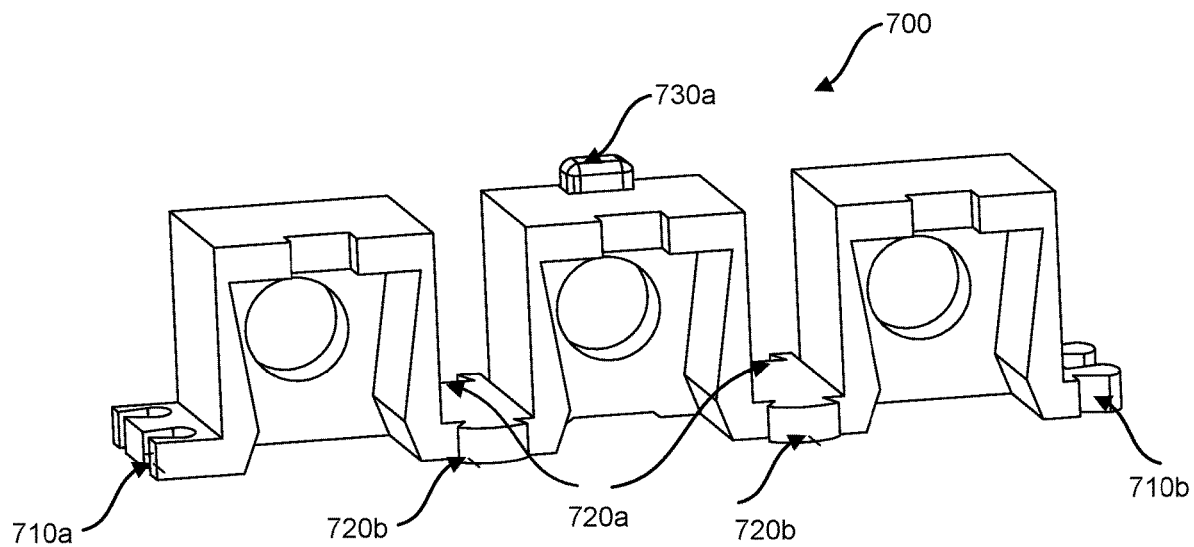
Figure 10A:
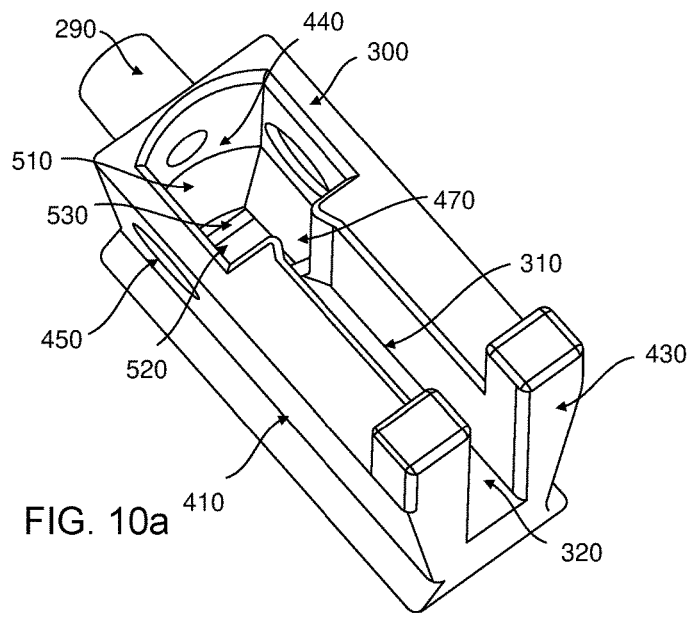
FIGS. 10a, 10b and 10c show a cell culture unit carrier according to embodiments of the invention.
Figure 10B:
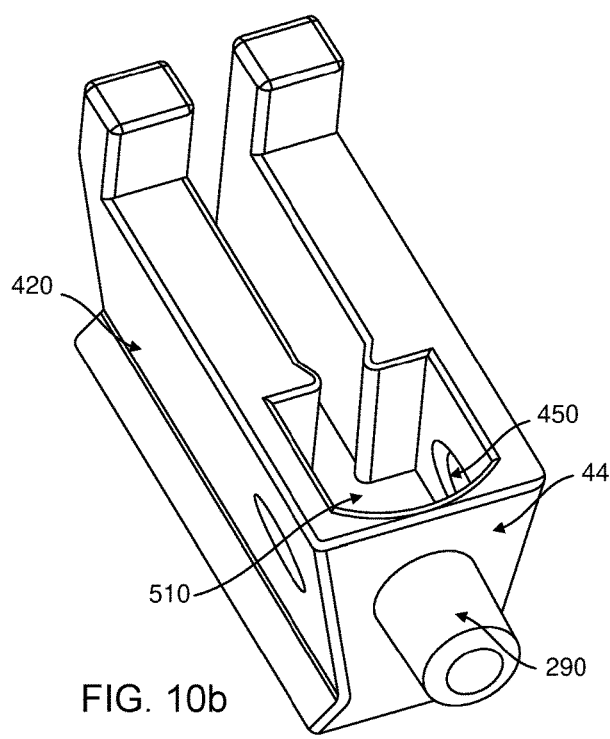

FIGS. 9a and 9b provide and illustration of the configuration of a cell cradle 300 of a single cell unit carrier in isolation of guide channel 310 (shown in FIG. 6); and FIGS. 10a and 10b illustrate the internal configuration of a complete single cell culture unit 400. Cell unit carrier 400 is formed from five walls including a rectangular planar left side wall 410 and a rectangular planar right side wall 420, each terminating toward the rear of the unit to join at 90 degrees with a planar rear outlet wall 430, and terminating toward the front of the unit to join at 90 degrees with a planar front inlet wall 440. The cell cradle illustrated in FIGS. 9a and 9b measures approximately 0.23 mm at its widest, and approximately 0.23 mm at its highest.

An annular protrusion from the exterior front surface of inlet wall 420 forms media inlet 290, having an external surface diameter approximately equal to (but slightly smaller than) the internal surface diameter of annular connector 230 (FIG. 6). The internal surface of front inlet wall 440 is curved horizontally to enable a pipette introduced into the cell cradle area through the channel outlet 320 and guide channel 310 to locate the centre point of the cell cradle area at the horizontal axis. The internal surface of left side wall 410, right side wall 420 and rear outlet wall 430 are generally flat. Left side wall 410 and right side wall 420 each comprise an overflow aperture 450 to allow for the overflow of media from the cell cradle 300, particularly when used for performing cellular perfusions. As illustrated in FIG. 9b, the lowest point of overflow aperture 450 is at the same height as the lowest point of guide channel 310 which ensures that excess fluid is preferentially moved away from the cell cradle area from the side of the cell culture unit rather than through the guide channel 310.

EXAMPLE 3

Cell Cover

FIG. 9c shows a cell cover unit 600 configured for linear array assembly with other cell cover units, and for housing a unitary cell cradle. The figure illustrates the 'puzzle piece' clip and lock system 610a and 610b which allows each of the cell cover units to engage each other in a linear array of infinite scalability. FIG. 9c also illustrates an embodiment of a cell cover unit which does not feature an aperture for access to the cell culture chamber rather relying on the slidable engagement of the cell carrier unit within to either cover or reveal at least a portion of the opening from above. This embodiment of the cell cover unit illustrates a notch 620 to be used for alignment with the cell cradle's inlet channel 470.

Figure 9E:
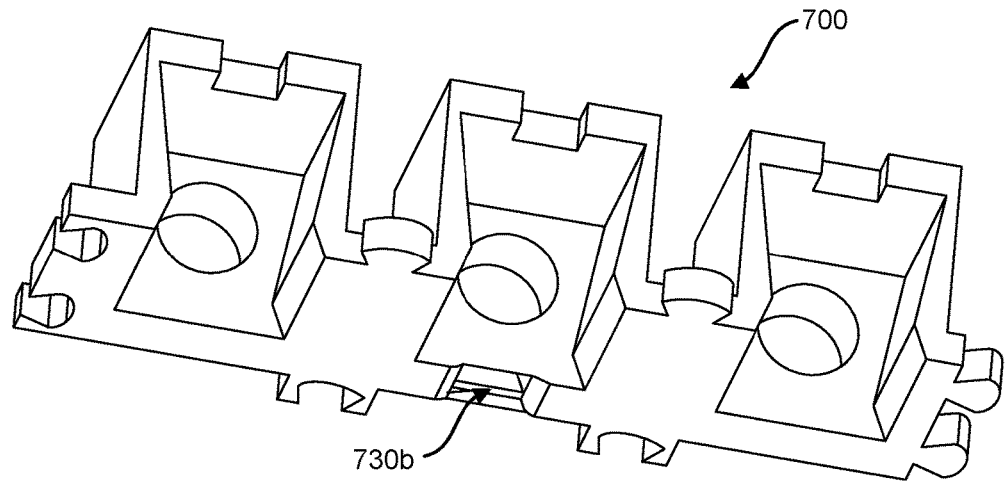

FIGS. 9d and 9e shows the cell cover units integrally arranged in a linear cell cover cartridge 700 with the further ability to form an array in three dimensions. To the left and the right of the cell cover cartridge the 'puzzle piece' clip and lock system 710a and 710b which maintains orientation with subsequent units allows arrays to be formed in these directions. A variation on this system 720a and 720b is also illustrated to the front and rear of the cell cover cartridge which similarly maintains orientation with subsequent units and allows arrays to be formed in these directions. Above the cell cover cartridge is a lug 730a which is configured to be received into a notch 730b of inverted shape below the cell cover cartridge to facilitate stacking in that direction.

FIGS. 10a and 10b (with FIGS. 9a and 9b) illustrate the placement of inner wall 460 dividing cell cradle 300 from guide channel 310 (FIGS. 10a and 10b). Inner wall 460 maintains a consistent height with respect to the front inlet wall 440, the left side wall 410, the right side wall 420 and rear outlet wall 430 so that array cover 120 (or a unit cover) rests flush across the top of the unit carrier, which is otherwise open from above. Inner wall 460 has a longitudinal inlet channel 470 formed therethrough. As illustrated in FIGS. 10a and 10b, the lowest point of inlet channel 470 is at level with the base of guide channel 310. Inlet channel 470 opens towards the rear of the unit carrier to the guide channel 310 and opens to the front of the unit carrier to the internal surface of the cell cradle 300. The internal surface of the cell cradle defines a cell culture cavity 510 for culturing and/or growing cells therein.

The size and shape of the cell culture cavity 510 is it governed by the maximum size of the embryo once developed to ensure the physical stability of the embryo contained therein. The size of the cell cradle 300 is approximately 0.23 mm×0.23 mm. The shape of the surface defining the cell cradle is generally rounded to conform to the general shape of the cell mass. In particular, each of the walls is downwardly tapered to give a more rounded internal shape to the cell cradle 300.

The position of cell culture cavity 510 is away from the flow of perfusion fluid. The aperture defined by the media inlet, the rear outlet wall, the guide channel, the longitudinal outlet channel, and the overflow apertures are generally in horizontal alignment, which define a fluid path. The position of the cell culture cavity is lower than the fluid path, which ensures that the cells within the cell cradle remain submerged in liquid media and are not physically agitated or otherwise disrupted by the current along the fluid path. The walls of the cell culture cavity terminate at a cell cradle base 520, which is generally formed in a horizontal plane, at a position lower with respect to the aperture defined by the media inlet, the rear outlet wall, the guide channel, the longitudinal outlet channel or the overflow apertures. The cell cradle base 520 also has a cell cradle outlet 530 which is closed whilst in use but may be released to drain fluid from within cell cradle 300.

Figure 10C:
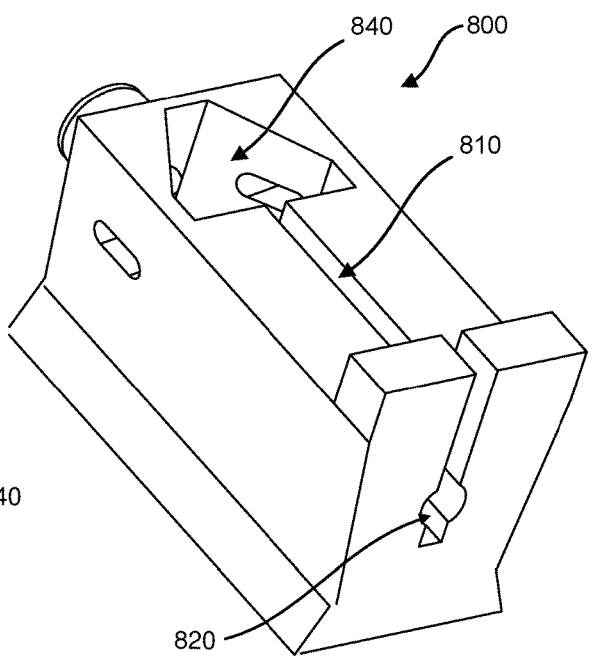

FIG. 10c illustrates alternative embodiments of cell carrier unit 800 features which include a narrowed guide channel 810, rounded channel inlet 820, and triangular footprint cell culture chamber 840. Narrowed guide channel 810 and rounded channel inlet 820 function in tandem to allow instruments to be guided and inserted into the cell culture chamber 840 without moving around or exiting through the narrowed guide channel, but still allowing for viewing of the instrument as it travels through the narrowed guide channel. The triangular footprint of the cell culture chamber 840 demonstrates other shapes which may be suitable for the cell culture chamber to take without the requirement of a curved proximal wall.

EXAMPLE 4

Cell Cover and Cell Carrier

Figure 10D:
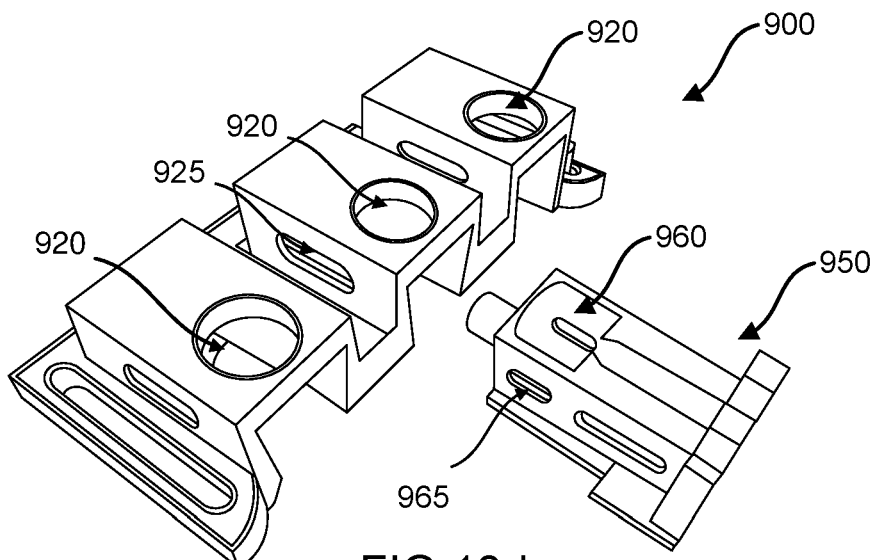
FIGS. 10d, 10e, and 10f provide top front perspective views of a cell culture unit carrier in three positions for engaging with a cell culture array.

FIGS. 10d, 10e, 10f, 10g, and 10h illustrate how a cell cover cartridge 900 according to embodiments engages with a cell carrier unit 950 according to embodiments. FIG. 10d shows a rear perspective view of the cell cover cartridge 900 and cell carrier unit 950 in unassembled form allowing the cell carrier unit to be inserted into the centre cover unit. FIG. 10d further illustrates the cell culture chamber 960 open from above, and the annular openings 920 configured to allow access therethrough. Each side of this embodiment of the cell culture chamber 960 features an overflow aperture 965 allowing potential overflow from the cell culture chamber through similarly located cover overflow apertures 925.

Figure 10E:
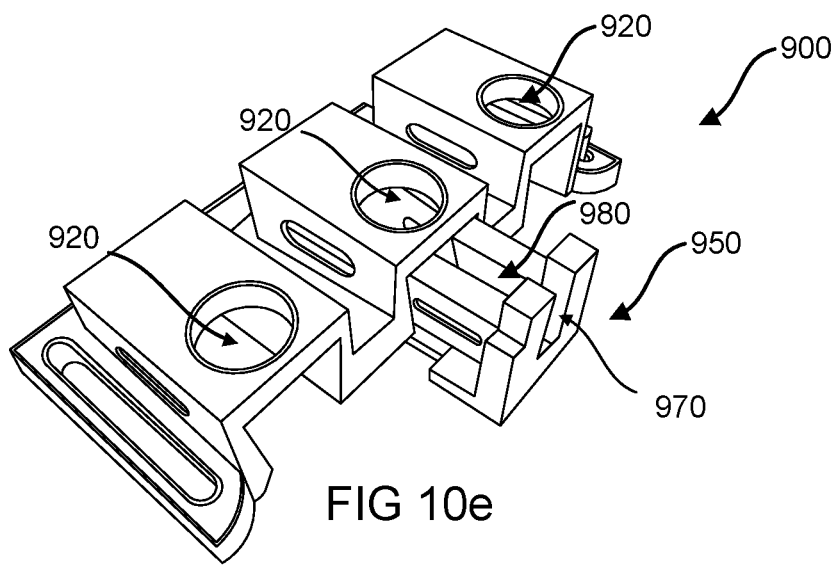
Figure 10F:
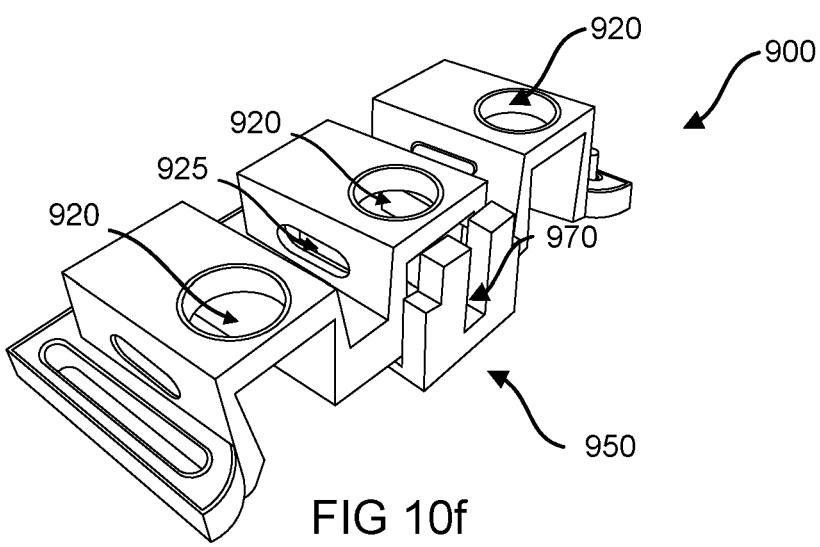
Figure 10G:
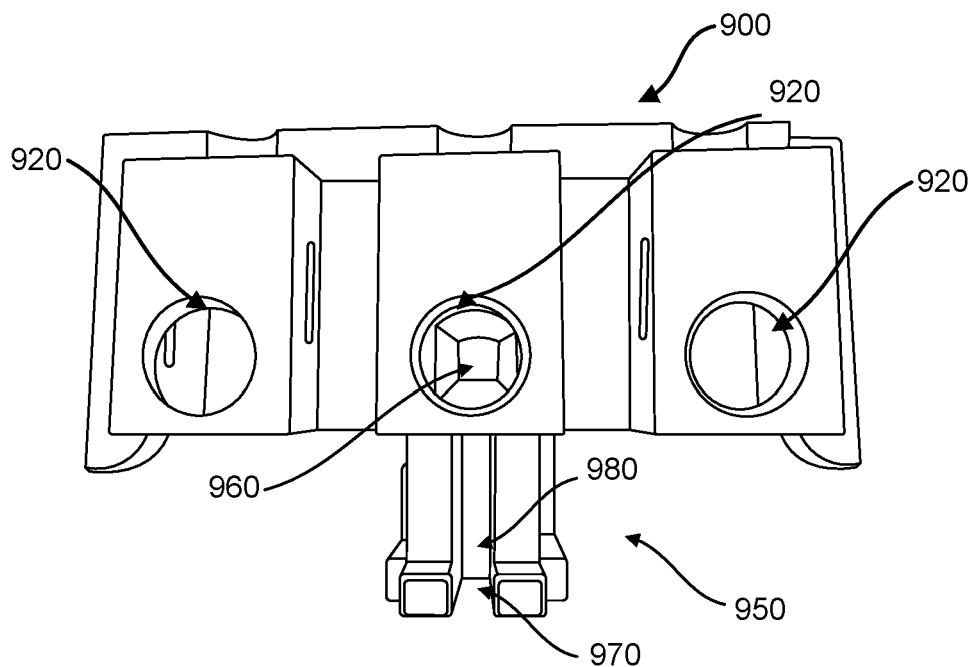
FIGS. 10g and 10h show a top perspective view of a cell culture unit carrier in two positions of engaging for introducing cells into the cell culture unit carrier.
Figure 10H:
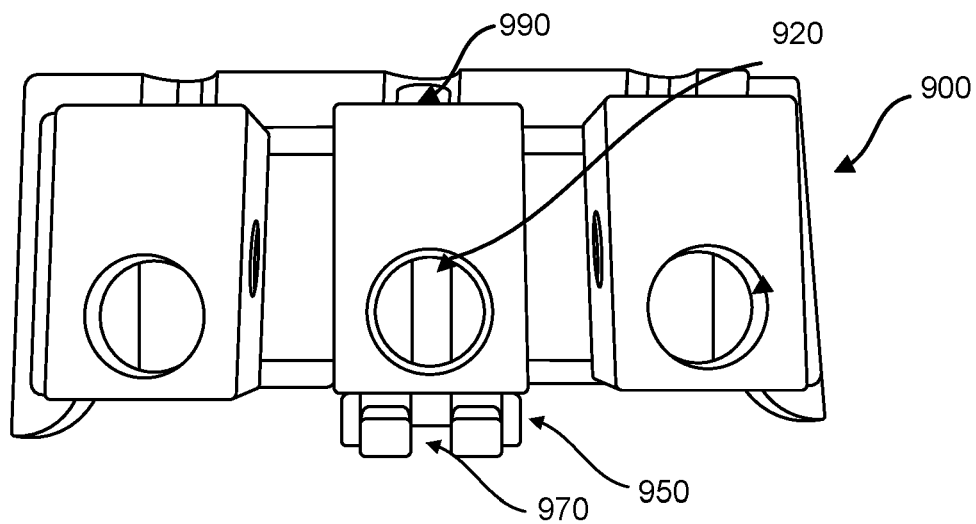

FIGS. 10e and 10g illustrate the cell cover cartridge 900 and cell carrier unit 950 partially engaged in a first position wherein the cell culture chamber 960 is accessible from above through the annular opening 920 for cell deposit, handling, and retrieval and the guide channel 980 is accessible both from above and via the channel inlet 970.

FIGS. 10f and 10g illustrate the cell cover cartridge 900 and cell carrier unit 950 fully engaged in a second position wherein the cell culture chamber 960 is covered by the cell cover cartridge 900 and the media inlet 990 is exposed through the front of the cell cover cartridge. In this position the overflow apertures 965 are contiguous with the cover overflow apertures 925 allowing overflow therethrough. Line of sight is maintained through the channel inlet and into the cell culture chamber 960 and through the media inlet 990.

Figure 11A:
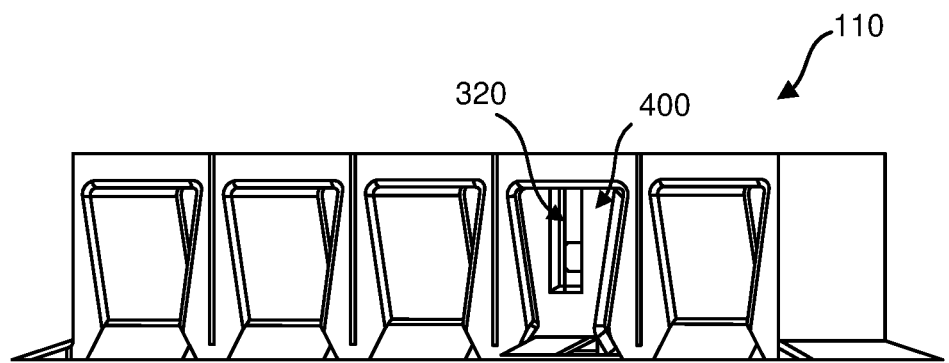
FIGS. 11a, 11b and 11c show a cell culture array or cartridge having a unit carrier located therein according to embodiments of the invention.
Figure 11B:
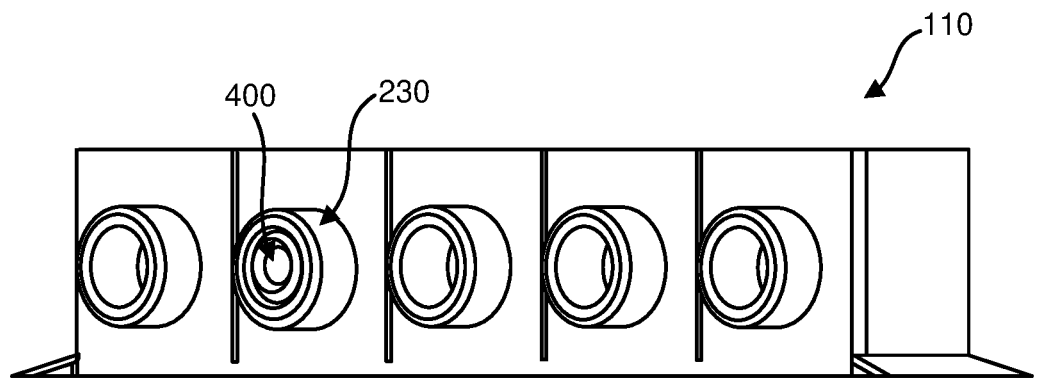
Figure 11C:
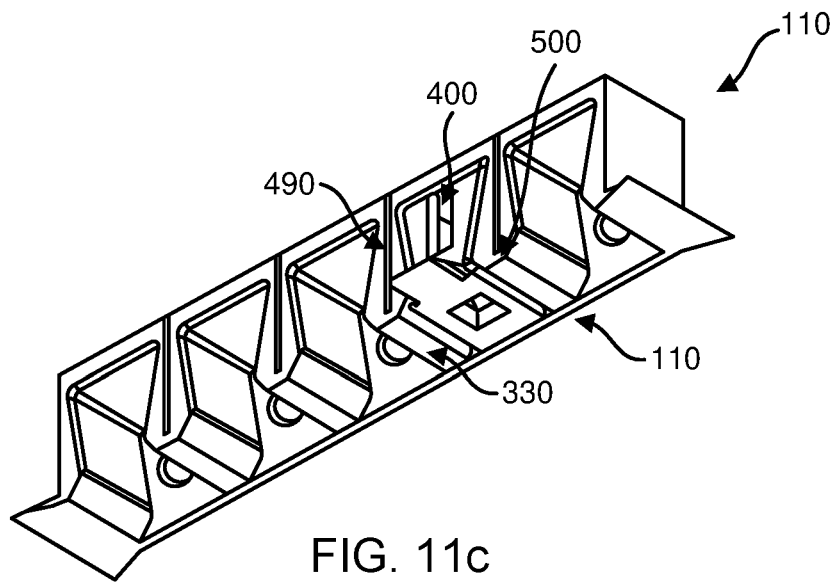

Turning to the external shape of carrier unit 400 as shown in FIGS. 10a and 10b, the left side wall 410 and right side wall 420 are joined to base wall 480 at about 100 degrees outwardly, whereas rear outlet wall 430 and front inlet wall 440 are joined to base wall 480 at 90 degrees. FIGS. 9a, 9b, 10a and 10b illustrate left sliding flange 490 and right sliding flange 500 protruding from base wall 480. The left and right side flanges 490 and 500 are shaped or otherwise configured to anchor the base of the unit carrier within or upon another object, or to slide upon or through another object. FIGS. 11a, 11b and 11c illustrate the placement of a unit carrier 400 within an array cover 110. FIG. 11a provides a rear view of the unit carrier 400 illustrating the positioning of channel outlet 320. FIG. 11b provides a front view of the unit carrier 400 illustrating the positioning of media inlet 290 within annular connector 230 of the array cover 110. FIG. 11c provides a bottom perspective view of the unit carrier 400 having left and right side flanges, 490 and 500 respectively, located in sliding engagement upon runners 330.

In certain embodiments slider 350, illustrated in FIG. 8, may be weakened to enable individual unit carriers of array carrier 120 to be snapped or broken (with or without a specialised tool) into individual unit carriers. Where array carrier 120 is configured to be broken down into individual unit carriers in this way, the array is configured to provide left and right side flanges upon breakage.

The capacity to break individual cell culture carriers or unit carriers away from an array may offer advantages to cellular processing for cryopreservation. For instance, individual units may be prepared in carrier for cryopreservation and stored as aliquots after breaking the unit away from the array, without any further physical manipulation of the cells.

Small batch manufacture of the above cell culture arrays can be performed using 3D printing techniques from biocompatible polymeric materials. Certain polymers have been shown to be printable biocompatible materials and have also been shown to be resistant to shattering when prepared for cryopreservation, for instance, a nanoscribe polymer or a crystal polystyrene.

EXAMPLE 5

Use of Cell Culture Array

Embodiments described herein may be used for cell culture of any kind, but may find particular use in the culture of mammalian cell lines. Embodiments described herein are particularly useful for cell cultures involving embryogenesis, and in turn, for their subsequent use in IVF procedures.

Embodiments may also be used for general cell culture, static perfusion, or active perfusion of cells in culture.

Figure 12:
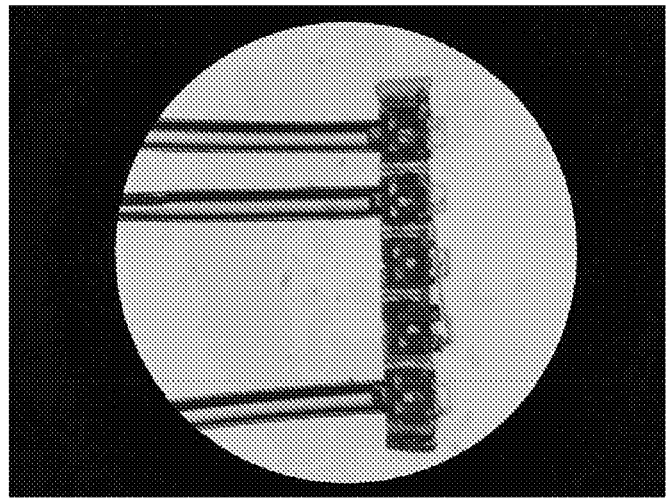
FIG. 12 shows a side view of a cell culture array or cartridge according to embodiments of the invention.

As illustrated in FIG. 12, a single cell culture unit may be used individually outside of an array configuration. A single silicon tube may be attached to the unit via the annular connector, which may be used to position or locate the unit where required. The tube may be used to fix the unit in position to observe cells during microscopy or to manipulate them using micropipettes or the like. The tube may be used to fix the position of the unit within a liquid medium which may be static or flowing (for instance, in a medium within a larger vessel where the unit is maintained and is being continuously perfused or replenished). The tube may also be connected to a pump or vacuum manifold to force fluid through the cell culture unit and perfuse the cell culture fluid maintained therein.

Figures 13A, 13B, 13C:
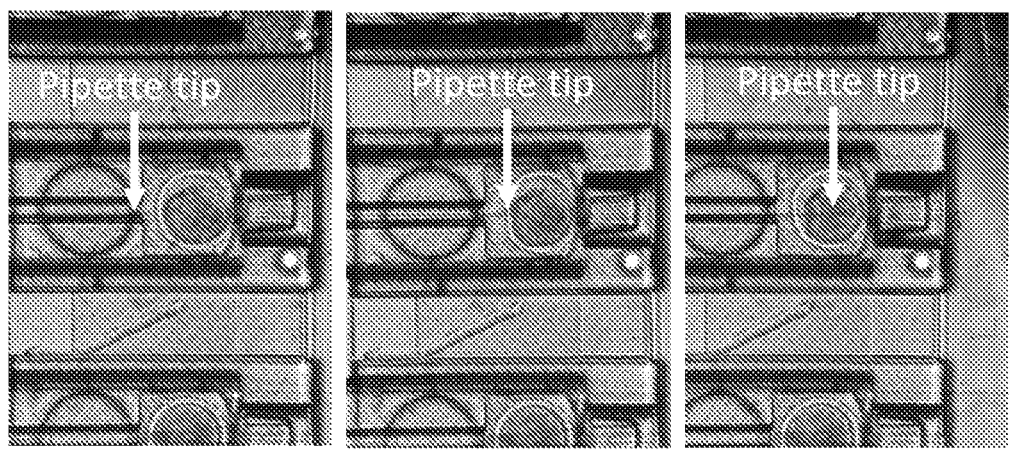
FIGS. 13a, 13b and 13c shows a side view of cell within a cell culture array or cartridge according to embodiments of the invention receiving a microinjection pipette.

As illustrated in FIG. 13, a cell culture array having five cell culture units within the array, a silicon tube having an internal diameter of 100 μm was attached to three of the five cell culture units. Media perfusion through each unit carrier was performed by passing the cell culture medium through each of the three units, while the other two units were not perfused.

Figure 14:
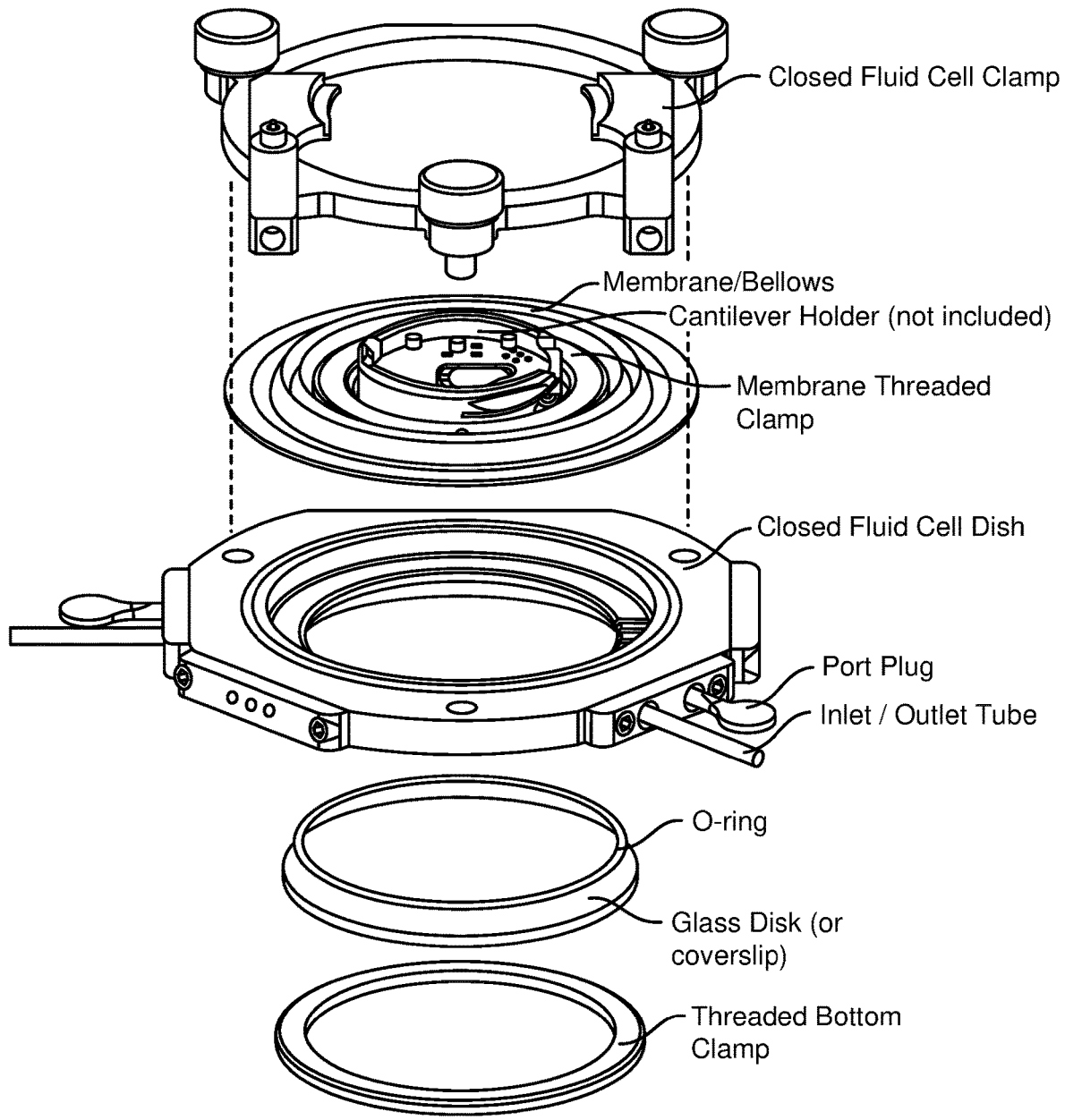
FIG. 14 shows an Atomic Force Microscope (AFM) mounting assembly for a cell culture microdevice according to embodiments of the invention.

FIG. 14 provides an assembly for retaining a cell culture array within an Atomic Force Microscope (AFM) mounting assembly. Variations to this assembly may be adopted for mounting the cell culture array within automation or other equipment, for example to adapt the mounting assembly for the user of laser, piezo injection, micro pumps, visually "trained" robotics, or other equipment that may reduce or remove manual intervention by embryologists during cell culture.

The assembly illustrated in FIG. 14 retains a petri dish base having a 35 mm diameter by 1 mm thick glass disc for mounting a cell culture array or cell culture unit therein, as illustrated in FIGS. 12 and 13. The petri dish may be specifically adapted to maintain the silicon tubing show in FIGS. 12 and 13 thereon, or they may simply be clamped in place. The petri dish is mounted with special mounts that can hold 12 mm or 25 mm circular cover slips for high NA inverted optical microscopy. The assembly allows cells maintained within arrays or units to be cultured and imaged in the petri dish.

The closed assembly illustrated in FIG. 14 provides a fitting for a petri dish upon the closed fluid cell clamp. The clamp is sealed against a membrane threaded clamp and is secured upon a closed fluid cell dish. Inlet and outlet access to the dish is provided via the port plug and inlet/outlet tubes provided through the closed fluid cell dish. The assembly is sealed against the threaded bottom clamp attached to the AFM by fitting an O-ring between the closed fluid cell dish and the glass disk. It is well known to persons skilled in the art where replacement of or use of additional O-rings, or the use of assembly tools, tweezers, and cleaning brushes is required to achieve a successful mount.

The cell culture array is designed for use in addition to a petri dish, microscope slide, or other culture plate. It does not substitute these devices but is used with these existing culture devices to locate a cell or aggregate of cells within such devices, to handle a cell or aggregate of cell without disturbing the cell(s), to more readily manipulate the cell(s) or to store the cell(s). The assembly described above is exemplary in nature and may be readily adapted to a particular use by a person skilled in the art. For instance, it is likely that certain users may prefer to place the microdevice on a slide which can be readily placed within the assembly described above in place of the petri dish.

The FIG. 14 assembly was implemented in a perfusion assembly for an enclosed and sealed array perfusion. The access ports were used for fluid and gas exchange for array perfusions via syringe injection, gravity feeding, and micro pump systems. The AFM mount may be adopted for time-lapse microscopy, embryo culture (with and without perfusion) and vitrification, in addition to fertilisation with or without Intracytoplasmic Sperm Injection (ICSI). Polymers, materials used and characteristics (The devices were microfabricated with a Nanoscribe GT Professional machine (Nanoscribe GmbH, Germany))

EXAMPLE 6

Design of In Vitro Studies

All experiments were approved by The University of Adelaide Animal Ethics Committee (M-2019-008) and were conducted in accordance with The Australian Code of Practice for The Care and Use of Animals for Scientific Purposes. Pre-pubertal CBA×C57B1/6 F1 hybrid and Swiss Albino female mice (3-4 weeks old) at 9-11 g were housed within the Laboratory Animal Services (University of Adelaide, Australia) under controlled temperature, 12 hours daylight cycle (12 hours light:12 hours dark) with water and feed ad libitum.

Pre-pubertal female mice were superovulated with 5 IU Equine chorionic gonadotropin (eCG; Folligon, Intervet, Boxmeer, The Netherlands) administered intra-peritoneal, 47 hours later mice were triggered with human chorionic gonadotropin (hCG; Humagon, Orgenon) administered intra-peritoneal.

Mice were then mated with a male (1 male:1 female) from the same strain and copulation plugs were checked the next day in the morning. 22 hours later post hCG, mice were culled via cervical dislocation and presumptive zygotes were harvested from the ampulla to be randomly allocated in each treatment group.

Media used in studies was sourced from ART Lab Solutions (Adelaide, Australia) including embryo wash and cleave media.

Microfabrication designs were developed in CAD and were microfabricated using a Nanoscribe GT Professional (Nanoscribe GmbH, Germany) using the manufacturers recommended polymers, materials, and settings.

All statistical analyses were performed using GraphPad Prism 8.0 (GraphPad Software, San Diego, California). Statistical analysis was performed to compare embryo development in standard embryo culture and embryo development in standard culture inside Pods docked inside Garages in the presence of other variables as described below. Normality testing was first performed in order to determine whether parametric or non-parametric testing should be used. Statistical significance of the difference in the mean between the groups was evaluated using an unpaired t test for normally distributed data or Kruskal-Wallis test for the non-normally distributed data. A P-value of <0.05 was considered as significant difference and a 10% difference was considered as biological significant.

EXAMPLE 7

Preliminary Analysis of Safety

Preliminary experiments were undertaken to investigate toxicity of the 3D printable polymer provided by Nanoscribe and used to construct the cell culture arrays and units, and to determine its potential impact on embryo development.

The following table provides the results of a first replicate of analyses of embryo development from Day 1 (zygote) and Day 2 (two-cell) embryo to Day 5 (blastocyst) following treatment.

|  | Day | | | | | Blastocyst rate (%) [From Cleave] |
|---|---|---|---|---|---|---|
|  | Day 1 (Zygotes) | Day 2 (2 cells) | Day 3 (6-8 cells) | Day 4 (Morula) | Day 5 (Blastocyst) | |
| In Vivo | — | — | — | — | 22 | |
| Treatment 1 | 20 | 20 | 20 | 20 | 20 | 100 [100] |
| Treatment 2 | 20 | 18 | 18 | 18 | 17 | 85 [94.44] |
| Treatment 3 | 40 | 36 | 36 | 36 | 33 | 82.5 [91.67] |
| Treatment 4 | 20 | 16 | 16 | 16 | 16 | 80.0 [100] |

In vivo: Blastocyst collection 94 hrs post hCG and mating
Treatment 1: Presumptive zygotes collected and cultured under standard embryo culture protocols using fresh cleavage media
Treatment 2: Presumptive zygotes collected and cultured in cleavage media used to wash the gadgets
Treatment 3: Presumptive zygotes collected and cultured in fresh cleavage media + gadgets
Treatment 4: Presumptive zygotes collected and cultured in cleavage media used to wash the gadgets + gadgets The following table provides the results of a second replicate of analyses of embryo development

|  | Day | | | | | Blastocyst rate (%) [From Cleave] |
|---|---|---|---|---|---|---|
|  | Day 1 (Zygotes) | Day 2 (2 cells) | Day 3 (6-8 cells) | Day 4 (Morula) | Day 5 (Blastocyst) | |
| In Vivo | — | — | — | — | — | |
| Treatment 1 | 20 | 17 | 17 | 12 | 12 | 60 [70.6] |
| Treatment 2 | 20 | 19 | 17 | 16 | 15 | 75 [78.95] |
| Treatment 3 | 30 | 21 | 20 | 20 | 20 | 66.70 [95.24] |
| Treatment 4 | 20 | 16 | 16 | 16 | 14 | 70 [87.5] |

In vivo: Blastocyst collection 94 hrs post hCG and mating
Treatment 1: Presumptive zygotes collected and cultured under standard embryo culture protocols using fresh cleavage media
Treatment 2: Presumptive zygotes collected and cultured in cleavage media used to wash the gadgets
Treatment 3: Presumptive zygotes collected and cultured in fresh cleavage media + gadgets
Treatment 4: Presumptive zygotes collected and cultured in cleavage media used to wash the gadgets + gadgets The following table provides the results of a third replicate of analyses of embryo development

|  | Day | | | | | Blastocyst rate (%) [From Cleave] |
|---|---|---|---|---|---|---|
|  | Day 1 (Zygotes) | Day 2 (2 cells) | Day 3 (6-8 cells) | Day 4 (Morula) | Day 5 (Blastocyst) | |
| In Vivo | — | — | — | — | — | |
| Treatment 1 | 20 | 13 | 13 | 13 | 13 | 65 [100] |
| Treatment 2 | 20 | 16 | 16 | 16 | 16 | 80 [100] |
| Treatment 3 | 30 | 20 | 20 | 20 | 20 | 66.70 [100] |
| Treatment 4 | 40 | 28 | 28 | 28 | 28 | 70 [100] |

In vivo: Blastocyst collection 94 hrs post hCG and mating
Treatment 1: Presumptive zygotes collected and cultured under standard embryo culture protocols using fresh cleavage media
Treatment 2: Presumptive zygotes collected and cultured in cleavage media used to wash the gadgets
Treatment 3: Presumptive zygotes collected and cultured in fresh cleavage media + gadgets
Treatment 4: Presumptive zygotes collected and cultured in cleavage media used to wash the gadgets + gadgets Further studies were undertaken whereby four carrier units were inserted in two array carriers. Embryo culture was performed in 20 μL cleave medium drops. Mouse embryos derived from hyperstimulated and mated female 4 week-old F1 CBAxC57816 mice were cultured for 24 hours from zygote to 2-cell stage. Results of 4 replicates of the zygote culture to blastocyst over 4 days, each having 40 replicates per group, showed no statistically significant difference in viability between cells cultured in the carrier unit versus those cultured in petri dish.

Figure 15A:
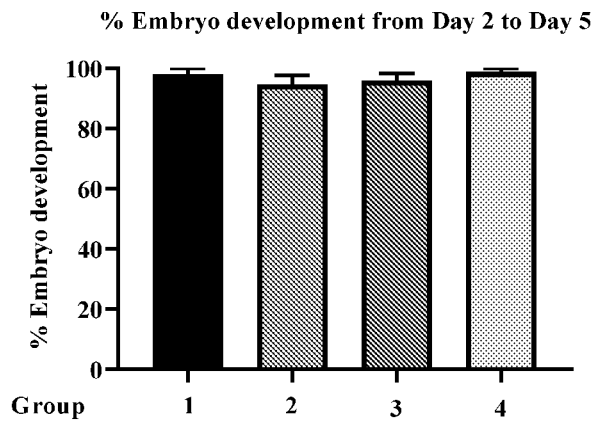
FIGS. 15a, 15b and 15c provides results of 3D printer polymer toxicity studies.

Results of 3D printer polymer toxicity studies are show in FIG. 15a, which shows the percentage CBAF1 mouse embryo development rate from cleaved embryos. In brief, 10 embryos were cultured in 204 drops of cleave media. For the treatment groups, embryos were cultured in apparatus produced using 3D printing techniques, which included 2 array covers and 10 unit carriers configured as 2×5 unit arrays. 10 embryos were placed within the 204 drop of cleavage media. Culture drops were covered with paraffin oil.

Embryos allocated to Group 1 were cultured in clean cleave medium (Control). Embryos in Group 2 were cultured in cleave medium previously exposed to 10 Pods and 2 Garages. Embryos in Group 3 were cultured in new cleave medium and were co-incubated with 10 Pods and 2 Garages per culture drop. Embryos in Group 4 were cultured in clean cleave medium and were co-incubated with 10 Pods and 2 Garages per drop.

Figure 15B:
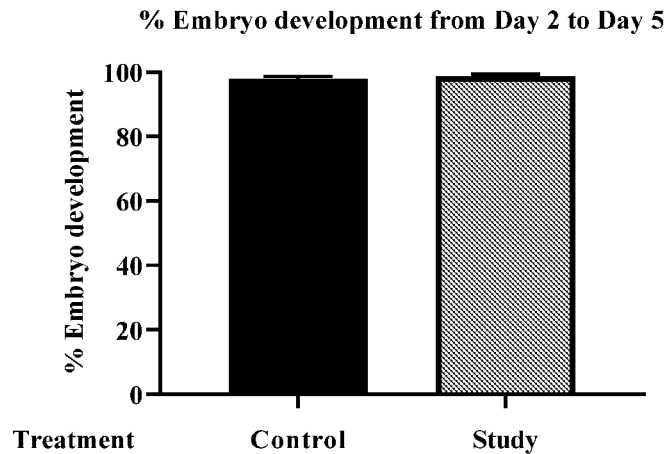

Percentage CBAF1 mouse embryo development from cleaved embryos is shown in FIG. 15b. Embryo culture was performed in 10 μL cleave medium drops. Embryos allocated to the Control treatment group were cultured in standard culture conditions and embryos allocated to the Study treatment group were cultured in standard culture conditions inside Pods docked in Garage. The Study treatment culture groups had 5 Pods and 1 Garage per drop (Mean±SEM).

Figure 15C:
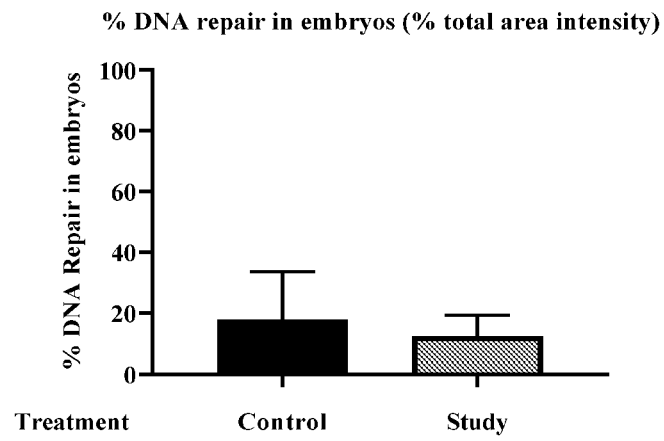

Percentage DNA repair on CBAF1 mouse embryo development is shown in FIG. 15c following γH2A.X DNA repair staining of blastocyst within the Control and Study Treatment Groups. Embryos allocated to the Control treatment group were cultured in standard culture conditions and embryos allocated to the Study treatment group were cultured in standard culture conditions inside Pods docked in Garage (Mean±SD).

In all studies, no significant difference was observed in the treatment groups. Toxicity of materials using in fabrication was not shown, indicating the likely safety of the microdevices.

EXAMPLE 8

Optimisation of Embryo Culture Conditions Within Cell Culture Unit

Figure 16:
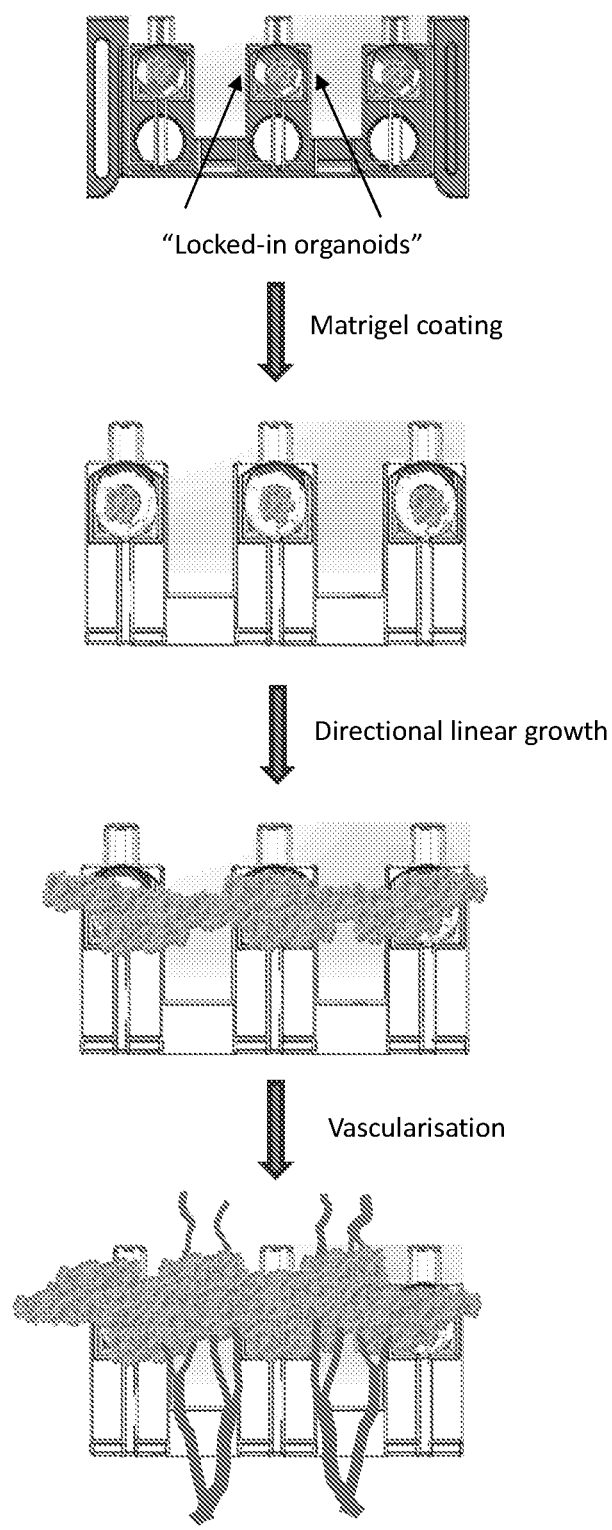
FIG. 16 provides a schematic diagram illustrating the vascularisation of tissues through the use of cell culture units according to embodiments.

FIG. 16 provides a schematic diagram illustrating the vascularisation of tissues achievable through the use of cell culture units according to embodiments. It is anticipated that under optimal conditions, organoids will successfully develop within the cell culture chamber. The chamber, coated with a Matrigel coating, provides a scaffold environment to promote the proliferation of adherent cells. Directional linear growth of the cell mass is provided through further apertures between the cell culture chamber and the external environment. The placement and size of the apertures through the unit carrier and the unit cover are selected to promote vascularisation to support in situ growth. These depend on the cell type and organoid type, and can be determined by persons skilled in the art.

Cell culture conditions were optimised for embryo development. Optimal culture media and air mixture were determined using methods that may be adapted for the optimisation of other conditions. Optimised cell culture conditions are anticipated to be transferrable to the proliferation of other cell types. Presumptive zygotes were harvested and randomly allocated to five treatment groups. Embryo development was observed and recorded daily.

Embryos were allocated to five groups each receiving a different culture medium treatment. For embryos allocated to Group 1, on-time developing embryos were moved to new cleave medium drops within the same dish. Embryos in Group 2 were placed in cleave medium and then were moved to a new dish with new cleave medium drops at Day 3. Embryos in Group 3 were placed in G1+ medium and viable embryos were moved to new G1+ medium drop within the same dish. Embryos in Group 4 were in G1+ medium and then were moved to a new G1+ medium drop at Day 3. Embryos in Group 5 were cultured in G1+ medium and were then moved to a new dish with G2+ medium drops. Embryo culture was carried out in a humidified oven-style conventional incubator at 6% $CO_2$, 5% $O_2$ and at 37° C. temperature.

Percent embryo developmental outcomes for embryos cultured within a standard 10 μL culture drop overlayed with oil in a petri dish are shown in FIG. 17. Group 1 embryos were cultured in ART Lab Solutions embryo cleave medium from Day 1 to Day 5. Group 2 embryos were cultured in ART Lab Solutions embryo cleave medium from Day 1 to Day 3 then embryos were moved to new ART Lab Solutions embryo cleave medium and were cultured to Day 5. Group 3 embryos were cultured in Vitrolife G1+ medium from Day 1 to Day 5. Group 4 embryos were cultured in Vitrolife G1+ medium from Day 1 to Day 3 and then embryos were moved to new Vitrolife G1+ medium and were cultured to Day 5. Group 5 embryos were cultured in Vitrolife G1+ medium from Day 1 to Day 3 and then were moved to new Vitrolife G2+ medium and were cultured to Day 5.

Embryo development was recorded daily; percentage embryo development for each treatment group is shown in FIG. 17. FIG. 17a shows percentage embryo development from Day 1 to Day 2, FIG. 17b shows percentage embryo development from Day 1 to Day 4, FIG. 17c shows percentage embryo development from Day 1 to Day 5 (Mean±SD). By Day 5, embryos cultured in Vitrolife G1+ medium followed by Vitrolife G2+ medium from Day 3 showed marked improvement in development.

Figure 17A:
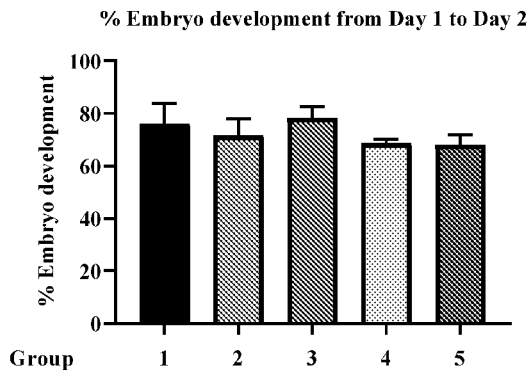
FIGS. 17a to 17e provide the results of cell culture optimisation studies.
Figure 17B:
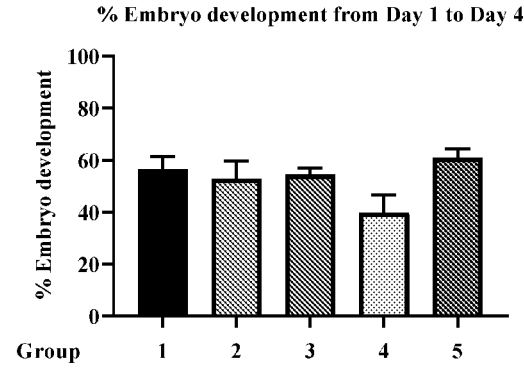
Figure 17C:
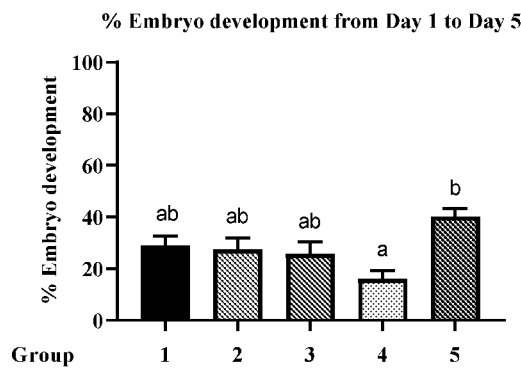
Figure 17D:
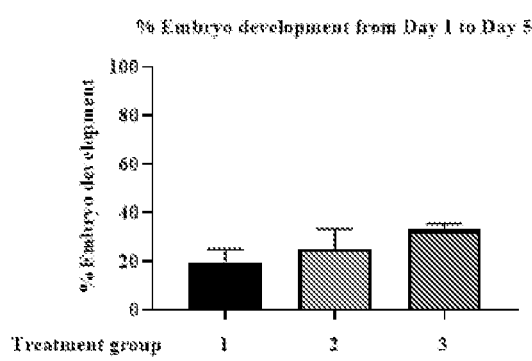

FIG. 17d provides the results of further studies in which cells were cultured within a cell unit carrier and covered by a cell unit cover. Group 1 embryos were cultured in Vitrolife G1+ medium from Day 1 to Day 5. Group 2 embryos were cultured in Vitrolife G1+ medium from Day 1 to Day 3 and then embryos were moved to new Vitrolife G1+ medium and were cultured to Day 5. Group 3 embryos were cultured in Vitrolife G1+ medium from Day 1 to Day 3 and then were moved to new Vitrolife G2+ medium and were cultured to Day 5. FIG. 17d shows percentage embryo development from Day 1 to Day 5 for each treatment group when cells were culture in devices according to the invention.

Figure 17E:
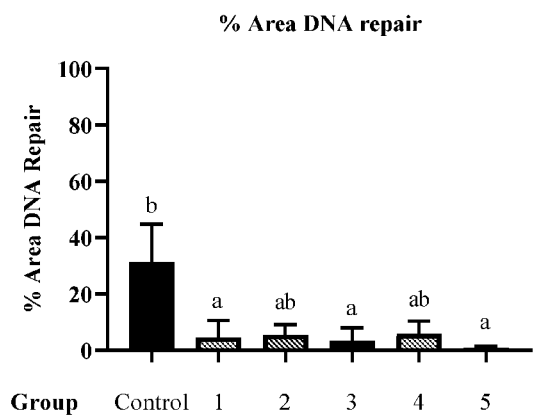

FIG. 17e shows percentage intensity of γH2a.x staining showing DNA repair in embryos cultured in standard 10 μL culture drop overlayed with oil in a petri dish (the controls were in vivo blastocysts). Group 1 embryos were cultured in ART Lab Solutions embryo cleave medium from Day 1 to Day 5. Group 2 embryos were cultured in ART Lab Solutions embryo cleave medium from Day 1 to Day 3 and then were moved to new ART Lab Solutions embryo cleave medium and were cultured to Day 5. Group 3 embryos were cultured in Vitrolife G1+ medium from Day 1 to Day 5. Group 4 embryos were cultured in Vitrolife G1+ medium from Day 1 to Day 3 and then were moved to new Vitrolife G1+ medium and were cultured to Day 5. Group 5 embryos were cultured in Vitrolife G1+ medium from Day 1 to Day 3 and then were moved to new Vitrolife G2+ medium and were cultured to Day 5 (Mean±SD).

Figure 17F:
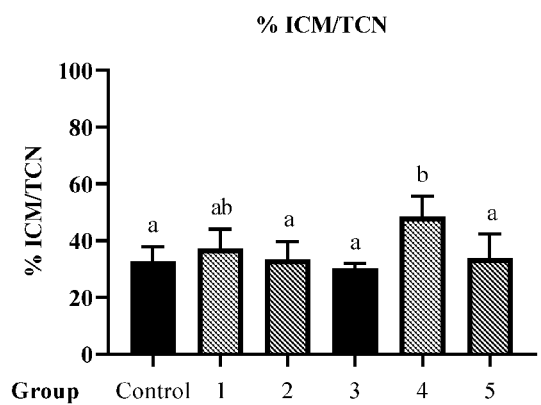
FIG. 17f shows internal cell mass for the same treatment groups.

FIG. 17f shows percent inner cell mass (ICM) over total cell number (TCN) in embryos cultured in standard 10 μL culture drop overlayed with oil in a petri dish (the controls were in vivo blastocysts). Group 1 embryos were cultured in ART Lab Solutions embryo cleave medium from Day 1 to Day 5. Group 2 embryos were cultured in ART Lab Solutions embryo cleave medium from Day 1 to Day 3 and were then moved to new ART Lab Solutions embryo cleave medium and were cultured to Day 5. Group 3 embryos were cultured in Vitrolife G1+ medium from Day 1 to Day 5. Group 4 embryos were cultured in Vitrolife G1+ medium from Day 1 to Day 3 and then were moved to new Vitrolife G1+ medium and were cultured to Day 5. Group 5 embryos were cultured in Vitrolife G1+ medium from Day 1 to Day 3 and were then moved to new Vitrolife G2+ medium and were cultured to Day 5 (Mean±SD).

DNA repair and percentage inner cell mass were improved for all treatment groups in which embryos were moved, with respect to those in the same culture medium that were not moved. For both DNA repair and percentage inner cell mass outcomes, embryos cultured in Vitrolife G1+ medium followed by Vitrolife G2+ medium showed improvements over embryos moved to Vitrolife G1+ medium at Day 3.

The poor development observed in embryos cultured in Vitrolife G1+ medium followed by Vitrolife G1+ medium was resolved by conducting further studies in which the same interventions were placed upon embryos cultured within cell unit carriers and cell unit covers. While Vitrolife G1+ medium followed by Vitrolife G2+ medium still showed optimal growth media conditions, cells cultured within cell unit carriers and cell unit covers also showed an improvement from a change in media over no change in media. The results show that the cell unit carriers and cell unit covers ameliorated the growth deficit from maintaining the same medium through the five day growth period.

Figure 18A:
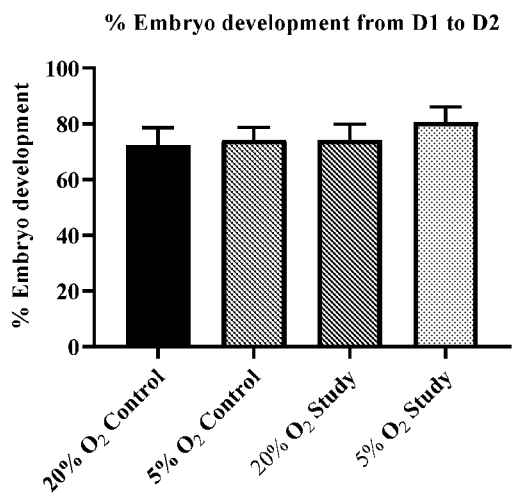
FIGS. 18a to 18d provide the results of oxygen optimisation studies.
Figure 18B:
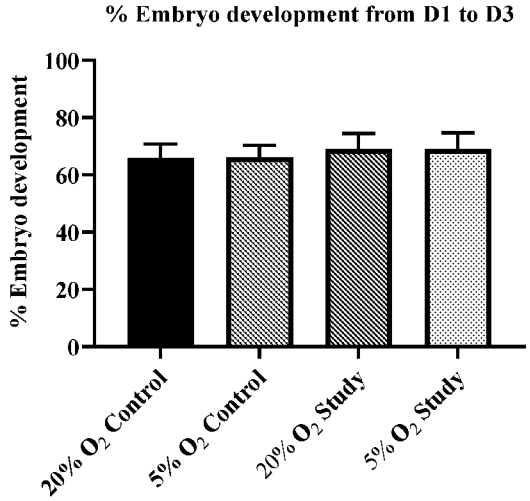
Figure 18C:
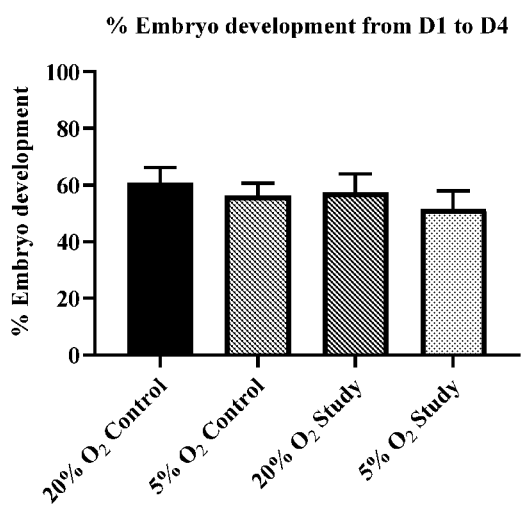
Figure 18D:
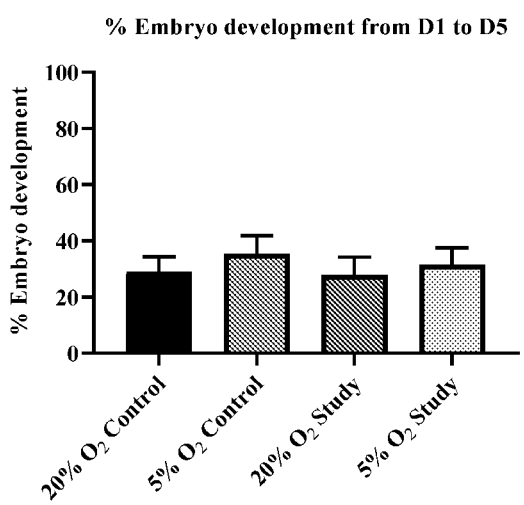
Figure 18E:
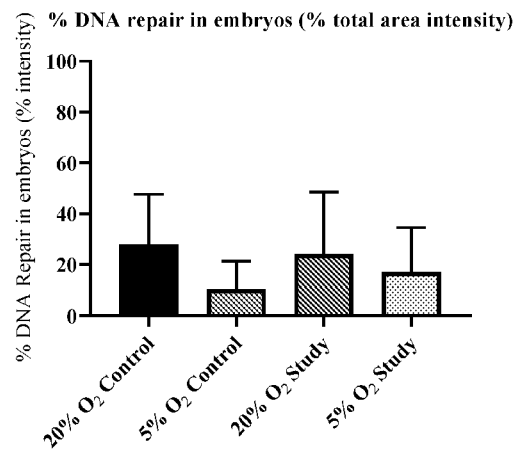
FIG. 18e shows percentage DNA repair within the same groups.

Percent embryo developmental outcomes for embryos cultured within a standard 10 µL culture drop overlayed with oil in a petri dish are shown in FIGS. 18a to 18d under an air mix of either 6% $CO_2$, 5% $O_2$, 89% $N_2$ or 6% $CO_2$, 20% $O_2$, 74% $N_2$ and under humidified conditions at 37° C. FIG. 18a shows percentage embryo development from Day 1 to Day 2, FIG. 18b shows percentage embryo development from Day 1 to Day 3, FIG. 18c shows percentage embryo development from Day 1 to Day 4, FIG. 18d shows percent embryo development from Day 1 to Day 5 (Mean±SD). FIG. 18e shows percentage intensity of γH2a.x staining showing DNA repair in embryos cultured in standard 10 µL culture drop overlayed with oil in a petri dish (the controls were in vivo blastocysts) with and without increased oxygen air mix.

While percentage embryo development showed a slight decline by Day 5 when embryos were cultured in 20% $O_2$ rather than 5% $O_2$, this result was not consistent through all days of culture. Percentage DNA repair, however, showed a marked improvement by Day 5 when cells were cultured in the presence of 20% $O_2$.

These results show that despite the trauma sustained by cells when they are disturbed during development, the replenishment of culture media has a significant improvement in the growth and viability of cultured cells. This improvement can be expected to increase by adopting continuous perfusion to introduce fresh culture media, and further still when the cells are not disturbed during perfusion. Inconsistencies in development and viability outcomes over time reflects the varying needs of the developing embryo at each growth stage. Static perfusion in the presence of optimised growth media and other culture conditions for each growth stage can be expected to improve growth outcomes further still.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The various apparatuses and components of the apparatuses as described herein, may be provided in various sizes and/or dimensions, as desired. Suitable sizes and/or dimensions will vary depending on the specifications of connecting components or the field of use, which may be selected by persons skilled in the art.

It will be appreciated that features, elements and/or characteristics described with respect to one embodiment of the disclosure may be used with other embodiments of the invention, as desired.

Although the preferred embodiments of the present disclosure have been disclosed for illustrative purposes, those skilled in the art will appreciate that various modifications, additions and substitutions are possible, without departing from the scope and spirit of the disclosure and accompanying claims.

It will be understood that when an element or layer is referred to as being "on" or "within" another element or layer, the element or layer can be directly on or within another element or layer or intervening elements or layers. In contrast, when an element is referred to as being "directly on" or "directly within" another element or layer, there are no intervening elements or layers present.

As used herein, the term "and/or" includes any and all combinations of one or more of the associated listed items.

It will be understood that, although the terms first, second, third, etcetera, may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section could be termed a second element, component, region, layer or section without departing from the teachings of the present disclosure.

Spatially relative terms, such as "lower", "upper", "top", "bottom", "left", "right" and the like, may be used herein for ease of description to describe the relationship of one element or feature to another element(s) or feature(s) as illustrated in the figures. It will be understood that spatially relative terms are intended to encompass different orientations of structures in use or operation, in addition to the orientation depicted in the drawing figures. For example, if a device in the drawing figures is turned over, elements described as "lower" relative to other elements or features would then be oriented "upper" relative the other elements or features. Thus, the exemplary term "lower" can encompass both an orientation of above and below. The device may be otherwise oriented (rotated 90 degrees or at other orientations) and the spatially relative descriptors used herein should be interpreted accordingly.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "including," "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Embodiments of the description are described herein with reference to diagrams and/or cross-section illustrations, for example, that are schematic illustrations of preferred embodiments (and intermediate structures) of the description. As such, variations from the shapes of the illustrations as a result, for example, of manufacturing techniques and/or tolerances, are to be expected. Thus, embodiments of the description should not be construed as limited to the particular shapes of components illustrated herein but are to include deviations in shapes that result, for example, from manufacturing.

Unless otherwise defined, all terms (including technical and scientific terms) used herein have the same meaning as commonly understood by one of ordinary skill in the art to which this description belongs. It will be further understood that terms, such as those defined in commonly used dictionaries, should be interpreted as having a meaning that is consistent with their meaning in the context of the relevant art and will not be interpreted in an idealised or overly formal sense unless expressly so defined herein.

Any reference in this specification to "one embodiment," "an embodiment," "example embodiment," etc., means that a particular feature, structure, or characteristic described in connection with the embodiment is included in at least one embodiment of the description. The appearances of such phrases in various places in the specification are not necessarily all referring to the same embodiment. Further, when a particular feature, structure, or characteristic is described in connection with any embodiment, it is within the purview of one skilled in the art to effect and/or use such feature, structure, or characteristic in connection with other ones of the embodiments.

Embodiments are also intended to include or otherwise cover methods of using and methods of manufacturing any or all of the elements disclosed above.

While the invention has been described above in terms of specific embodiments, it is to be understood that the invention is not limited to these disclosed embodiments. Upon reading the teachings of this disclosure many modifications and other embodiments of the invention will come to the mind of those skilled in the art to which this invention pertains, and which are intended to be and are covered by both this disclosure and the appended claims.

All publications mentioned in this specification are herein incorporated by reference. Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia or elsewhere before the priority date of each claim of this application.

It is indeed intended that the scope of the invention should be determined by proper interpretation and construction of the appended claims and their legal equivalents, as understood by those skilled in the art relying upon the disclosure in this specification and the attached drawings.

CITATIONS

1. Data on IVF clinics show wide variation in success rate, BMJ 2002; 325 doi: https://doi.org/10.1136/bmj.325.7362.460/e (Published 31 Aug. 2002).
2. JMST Advances, June 2019, Volume 1, Issue 1-2, pp 1-111 Cite as Microfluidic technology for in vitro fertilization (IVF).

The invention claimed is:

1. A cell culture microdevice for maintaining and culturing a cell therein comprising;
   a cell culture unit having at least a first cell carrier unit defining a cell culture chamber formed therein,
   the first cell carrier unit formed from at least,
      a chamber base shaped to support the cell thereon, and one or more chamber walls having one or more chamber wall surfaces enclosing the cell culture chamber about a chamber boundary,
      the first cell carrier unit further providing a guiding surface to guide instruments or fluids into the cell culture chamber located at an aperture through a chamber wall,
   wherein the dimensions of the cell culture microdevice are between approximately 0.1 µm and approximately 1000 µm in width, height and length,
   wherein the cell culture microdevice is configured to be maintained in a liquid medium within a larger vessel and to enable the passive exchange of liquid fluids with the larger vessel, and
   the cell culture microdevice is configured at a scale to substantially enclose a single cell or cell mass therein.

2. The cell culture microdevice of claim 1 wherein the one or more chamber walls comprises one or more inner wall surfaces sloped towards a proximal point of the chamber and are configured to guide the placement of an instrument or a cell within the culture chamber.

3. The cell culture microdevice of claim 1 wherein the cell culture chamber is open from above and the chamber base comprises a curved inner surface.

4. The cell culture microdevice of claim 1 wherein the one or more chamber walls comprises;
   a proximal wall having a curved inner wall surface configured to guide the placement of an instrument within the culture chamber, and
   a distal wall defining a distal chamber boundary and having the aperture through the chamber wall formed therethrough, the aperture defining an opening in communication with an elongated guiding portion projecting outwardly from the cell culture chamber having a channel formed therein providing the guiding surface to guide instruments or fluids into the cell culture chamber.

5. The cell culture microdevice of claim 4 wherein the one or more chamber walls comprises at least a left side wall and a right side wall each having a left side aperture and a right side aperture formed therethrough.

6. The cell culture microdevice of claim 4 wherein the proximal wall has a proximal aperture formed therethrough, configured in horizontal alignment with the guiding surface to ease the flow of fluid through the cell culture chamber between the aperture and the proximal aperture.

7. The cell culture microdevice of claim 6 wherein the proximal wall comprises a perfusion inlet opening adapted for fluid perfusion therethrough, and a tubing fitting configured for engagement of a perfusion tube to the perfusion inlet opening.

8. The cell culture microdevice of claim 1 wherein the first cell carrier unit comprises a cell chamber wall having an exterior wall coupling adapted to engage with a corresponding exterior wall coupling on at least a second cell carrier unit, thereby forming a cell carrier array.

9. The cell culture microdevice of claim 1 further comprising at least a second cell carrier unit formed integrally with the first cell carrier unit, thereby forming a cell carrier cartridge.

10. The cell culture microdevice of claim 9 further comprising a first cell cover unit having a first cover wall configured to cover at least a portion of the opening from above of the cell culture chamber when the first cell cover unit and the first cell carrier unit are connected to form a cell culture unit base.

11. The cell culture microdevice of claim 10 wherein the first cell cover unit comprises an exterior wall coupling adapted to engage with a corresponding exterior wall coupling on at least a second cell cover unit, thereby forming a cell cover array.

12. The cell culture microdevice of claim 11 further comprising at least a second cell cover unit formed integrally with the first cell cover unit, thereby forming a cell cover cartridge.

13. The cell culture microdevice of claim 12 wherein the first cell cover unit further comprises an access aperture formed therethrough, the access aperture formed through the first cell cover unit is configured to permit access to the opening from above in a first position and cover at least a portion of the opening from above in a second position, and is adapted to slidably engage the first cell carrier unit from the first position to the second position.

14. The cell culture microdevice of claim 1 wherein an exterior surface of the chamber base comprises a notch configured to receive a lug projecting outwardly from a cell carrier unit or a cell cover unit.

15. A method of use of the cell culture microdevice of claim 1 comprising the steps of; placing at ease one cell within the cell culture chamber of the cell culture microdevice, and culturing the cell therein.

16. A method of use of the cell culture microdevice of claim 1 comprising the steps of; obtaining instructions for constructing the cell culture microdevice, and executing the instruction in an additive manufacturing process.

* * * * *